US006688123B2

(12) United States Patent
Felder et al.

(10) Patent No.: US 6,688,123 B2
(45) Date of Patent: Feb. 10, 2004

(54) AUTOMATED STORAGE AND RETRIEVAL APPARATUS FOR FREEZERS AND RELATED METHOD THEREOF

(75) Inventors: Robin A. Felder, Charlottesville, VA (US); B. Sean Graves, Charlottesville, VA (US); James P. Gunderson, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 10/429,490

(22) Filed: May 5, 2003

(65) Prior Publication Data

US 2003/0196444 A1 Oct. 23, 2003

Related U.S. Application Data

(63) Continuation of application No. 10/263,910, filed on Oct. 3, 2002, now Pat. No. 6,581,395, which is a continuation of application No. 09/935,488, filed on Aug. 23, 2001, now Pat. No. 6,467,285.
(60) Provisional application No. 60/299,597, filed on Jun. 20, 2001, and provisional application No. 60/227,166, filed on Aug. 23, 2000.

(51) Int. Cl.$^7$ .......................... F25D 17/00; F25D 25/02
(52) U.S. Cl. ............................... 62/177; 62/381
(58) Field of Search ...................... 62/177, 381, 382, 62/378, 62, 178, 336, 337; 434/322; 600/544

(56) References Cited

U.S. PATENT DOCUMENTS

| | | | | | |
|---|---|---|---|---|---|
| 3,163,994 A | * | 1/1965 | Haumann et al. | .............. | 62/218 |
| 3,782,133 A | * | 1/1974 | Desperier et al. | ............. | 62/381 |
| 3,787,699 A | * | 1/1974 | Menachem et al. | ......... | 250/507 |
| 4,485,641 A | * | 12/1984 | Angelier et al. | .......... | 62/514 R |
| 4,799,358 A | * | 1/1989 | Knopf et al. | ..................... | 62/3 |
| 4,870,829 A | * | 10/1989 | Oullette et al. | .............. | 62/51.1 |
| 4,969,336 A | * | 11/1990 | Knippscheer et al. | ......... | 62/266 |
| 5,125,240 A | * | 6/1992 | Knippscheer et al. | ......... | 62/266 |
| 5,176,202 A | * | 1/1993 | Richard | ...................... | 165/48.1 |
| 5,233,844 A | * | 8/1993 | Knippscheer et al. | ......... | 62/440 |
| 5,498,116 A | * | 3/1996 | Woodruff et al. | ........... | 414/331 |
| 5,628,197 A | * | 5/1997 | Rada | .............................. | 62/62 |
| 5,638,686 A | * | 6/1997 | Coelho et al. | ............... | 62/51.1 |
| 5,921,102 A | * | 7/1999 | Vago | .......................... | 62/337 |
| 6,068,437 A | * | 5/2000 | Boje et al. | ............. | 414/331.02 |

FOREIGN PATENT DOCUMENTS

| | | | | | |
|---|---|---|---|---|---|
| EP | 0411224 A2 | * | 2/1991 | ............ | F25D/3/11 |
| WO | WO 91/02202 | * | 2/1991 | .......... | F25D/23/02 |
| WO | WO 98/58215 | * | 12/1998 | .......... | F25B/19/00 |

* cited by examiner

Primary Examiner—Marc Norman
(74) Attorney, Agent, or Firm—Robert J. Decker

(57) ABSTRACT

An automated cold storage apparatus, and related method thereof, provides a sample process management system that is a revolutionary approach to the storage and retrieval regarding critical samples. The system—a significant technological breakthrough in laboratory automation—is the first ultra low temperature robotic system capable of being validated. Samples in containers are stored and retrieved robotically through an airlock climate-control chamber that is automatically dehumidified by a dry gas purge, such as a carbon dioxide or nitrogen purge or the like. This purge rapidly reduces ambient humidity to a desirable relative humidity (RH), e.g., less than about 15% RH, virtually eliminating the accumulation of frost. Microplates are systematically identified using barcode technology, for example. Once through the climate-controlled chamber, the containers (i.e., samples) are robotically transferred to the rotary mechanism. This mechanism transports the containers to a derived nest location upon the storage means, such as a carousel or to one of the stationary addresses.

42 Claims, 26 Drawing Sheets

AUTOMATED STORAGE AND RETRIEVAL APPARATUS FOR FREEZERS AND RELATED METHOD THEREOF

RELATED APPLICATIONS

This application is a continuation of application Ser. No. 10/263,910, filed Oct. 3, 2002, issued Jun. 24, 2003, as U.S. Pat. No. 6,581,395, the entire disclosure of which is hereby incorporated by reference herein, which is a continuation of application Ser. No. 09/935,488, filed Aug. 23, 2001, issued Oct. 22, 2002, U.S. Pat. No. 6,467,285, the entire disclosure of which is hereby incorporated by reference herein, which claims priority from U.S. Provisional Application Ser. No. 60/227,166, filed on Aug. 23, 2000, entitled "Automated Storage and Retrieval Apparatus for Freezers and Related Method Thereof," and 60/299,597, filed on Jun. 20, 2001, entitled "Automated Storage and Retrieval Apparatus for Freezers and Related Method Thereof," the entire disclosures of which are hereby incorporated by reference herein.

FIELD OF INVENTION

This invention relates to an automated storage and retrieval apparatus for ultra low temperature freezers, and more particularly an apparatus that improves the overall quality of the climate associated with storing items therein.

BACKGROUND OF INVENTION

Advancements in biotechnology and medical science require the analysis of ever-increasing numbers of various biological samples. Many biological samples must be stored at below-freezing temperatures in order to preserve them for future reference, analysis, or use. For example, DNA, RNA, cells and protein samples, as well as the reagents necessary for conducting various analyses of these samples, must be stored at ultra-cold temperatures to prevent degradation that would interfere with reliable analyses of the biological products.

Storage below $-80°$ C. is generally required for successful preservation of biomolecules, cells, and tissue (morphology and viability) for extended periods of time. However, shelf life and the ability to recover living cells are dramatically improved at about $-196°$ C. ($-196°$ C. being the boiling point of liquid nitrogen). The National Institute of Standards and Technology has suggested that the term cryogenics be applied to all temperatures below $-150°$ C. ($-238°$ F. or $123°$ above absolute zero on the Kelvin scale). Some scientists regard the normal boiling point of oxygen ($-183°$ C. or $-297°$ F.), as the upper limit. The term ultra low temperature is probably not officially recognized by any standards body. However, it is generally agreed that a freezer refers to a storage device that operates from about $-5°$ C. to $-20°$ C., an ultra low operates from about $-50°$ C. to about $-90°$ C., and a cryogenic freezer operates from about $-140°$ C. to $-196°$ C.

There are many problems associated with placement and retrieval of samples from ordinary laboratory freezer compartments. For instance, in an ordinary freezer compartment, containers of samples must be stored in front of and on top of each other to maximize use of the available space. Even if the containers are of standard sizes, and therefore easily stackable and even if a positional inventory of the samples is kept, it is still necessary to shuffle the containers around manually in order to retrieve a desired container. This is problematic because it requires keeping the freezer door open for possibly extended periods of time. Keeping the freezer door open causes the interior temperature of the freezer compartment to rise temporarily, which can cause thawing of samples housed near the door of the freezer. Once the freezer is closed and the temperature decreases, the samples refreeze. This repeated freezing and thawing can cause more rapid degradation of samples. Keeping the freezer door open also allows frost to build up in the freezer compartment. With repeated openings of the door, the frost eventually can freeze containers to the bottom of the freezer compartment or to each other. As a result, the door must be kept open longer in order to break containers out of the frost, which only exacerbates the problem.

The increasing need for high quality bio-repositories in hospitals, research institutions, and pharmaceutical clinical research laboratories provides a market for automated ultra-cold storage devices that will improve sample quality, organize storage, provide rapid access to all specimens, and maintain electronic records of all specimens stored within the container.

U.S. Pat. No. 5,921,102 to Vago, herein incorporated by reference, utilizes a storage apparatus particularly with automatic insertion and retrieval. Drawbacks of the Vago approach, but not limited thereto, are that it fails to provide the climate control associated with the freezer and the various interchanging devices, and other features and aspects.

There is therefore a need in the art for an automated cold storage apparatus, and related method thereof, that can provide, among other things a more organized storage and retrieval apparatus, less accumulation of moisture and frost within the cold storage compartment, less temperature fluctuation from sample withdrawal, and rapid random access to all specimens.

SUMMARY OF THE INVENTION

The present invention automated cold storage apparatus, and related method thereof, provides a sample process management system that is a revolutionary approach to the storage and retrieval of critical samples. The system—a significant technological breakthrough in laboratory automation—is the first ultra low temperature robotic system capable of being validated. Samples in containers are stored and retrieved robotically through an airlock climate-control chamber (access means) that is automatically dehumidified by a dry gas purge, such as a carbon dioxide or nitrogen purge or the like. This purge rapidly reduces ambient humidity to a desirable relative humidity (RH), e.g., less than about 15% RH, virtually eliminating the accumulation of frost. Microplates or storage containers, or the like, are systematically identified using barcode technology, for example. Once through the climate-controlled chamber, the containers (i.e., samples) are robotically transferred to the rotary mechanism. This mechanism transports the containers to a derived nest location upon the storage means, such as a carousel or one of the stationary addresses. For illustrative purposes only, the carousel and stationary nests may have a combined capacity of 1,000 standard microplates. It is contemplated that various capacities may be designed.

The preferred embodiments of the present invention automated storage and retrieval apparatus, and related method thereof, operate at an ultra low temperature of about $-50°$ C. to about $-90°$ C. It should be understood that the apparatus may operate in a range of $-50°$ C. up to ambient temperature or greater. The normal design operating temperature of the freezer compartment of the present invention is about $-80°$ C. It should be noted that the present invention is contemplated to operate at conditions colder than ultra low temperatures in the range of about −140° C. to about −90° C. Conveniently, if the freezer fails for whatever reason—maintenance or scheduled outage—then liquid carbon dioxide can be pumped into the system and keep it at approximately −78° C. The ultra low freezer set point (approximately 78° C.) of the apparatus can be backed up by installing a cylinder of liquid carbon dioxide.

In one aspect, the present invention features an automated storage and retrieval apparatus for storing containers at ultra low temperatures or other preferred temperatures. The apparatus comprising: a freezer compartment, the freezer compartment having a side wall; a storage carousel disposed inside the freezer compartment for holding the containers; a climate-controlled chamber disposed on the side wall; a climate system for controlling the climate of the chamber; and an interchange mechanism configured. The interchange mechanism is configured to: interchange a container between the interchange mechanism and the climate-controlled chamber while in a chamber exchange position, and interchange a container between the interchange mechanism and the carousel while in a carousel exchange position. The chamber also being configured to: isolate the container from the interchange mechanism as container is deposited from the exterior or placed into the exterior, and isolate the container from the exterior as container is exchanged between the chamber and the interchange mechanism.

In some embodiments, the carousel can be replaced with a stationary storage rack, and additional storage racks may be added. The interchange mechanism is configured to interchange a container between the interchange mechanism and the rack(s) while in a rack exchange position(s).

In a second aspect, the present invention provides an automated storage and retrieval apparatus for storing containers at ultra low temperatures or other preferred temperatures. The apparatus comprising: a freezer means for freezing the containers; a storage means disposed inside the freezer means for holding the containers; a chamber means for interchanging the containers between the exterior and the freezer means; a climate system control means for controlling the climate of the chamber means; and an interchange means. The interchange means for: interchanging a container between the interchange means and the chamber means while in a chamber exchange position, and interchanging a container between the interchange means and the storage means while in a storage exchange position. The chamber means for: isolating the container from the interchange means as container is deposited from the exterior or placed into the exterior, and isolating the container from the exterior as container is exchanged between the chamber means and said interchange means.

In a third aspect, the present invention provides a method for automatically depositing and storing containers, as well as a method for storing and retrieving containers in a freezer compartment of an automated apparatus. The apparatus comprising: a freezer means for freezing the containers; a storage means disposed inside the freezer means for holding the containers; a chamber means for interchanging the containers between the exterior and the freezer means; a climate system control means for controlling the climate of the chamber means; and an interchange means. The interchange means for: interchanging a container between the interchange means and the chamber means while in a chamber exchange position, and interchanging a container between the interchange means and the storage means while in a storage exchange position. The chamber means for: isolating the container from the interchange means as container is deposited from the exterior or placed into the exterior, and isolating the container from the exterior as container is exchanged between the chamber means and said interchange means.

An advantage of the present invention automated storage and retrieval apparatus for ultra low temperature freezers, and related method thereof, is that the apparatus can operate in a stand-alone mode or can be integrated into a completely automated laboratory. It is scalable to meet the needs of small laboratories as well as large institutions that will require long-term storage of large numbers of samples.

Another advantage of the present invention is that the apparatus can be designed as a slide-in unit for existing ultra-cold freezers, which will keep the majority of the hardware in the door so as to be insulated from the freezer compartment, minimizing both the number of low-temperature hardware components and the actual alteration to the freezer itself A reduced number of moving components is continuously exposed to the design temperature of about −80° C., reducing the cost of production.

Further advantages of the present invention are attributed to the improved sample quality, lowered operating costs, and reduced maintenance of the automated storage and retrieval apparatus.

Finally, an advantage of the present invention is that it provides ultra-low temperature automation or lower and user-friendly information technology in a proven reliable manner.

These and other objects, along with advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DETAILED DESCRIPTION OF THE INVENTION

Figure 1:
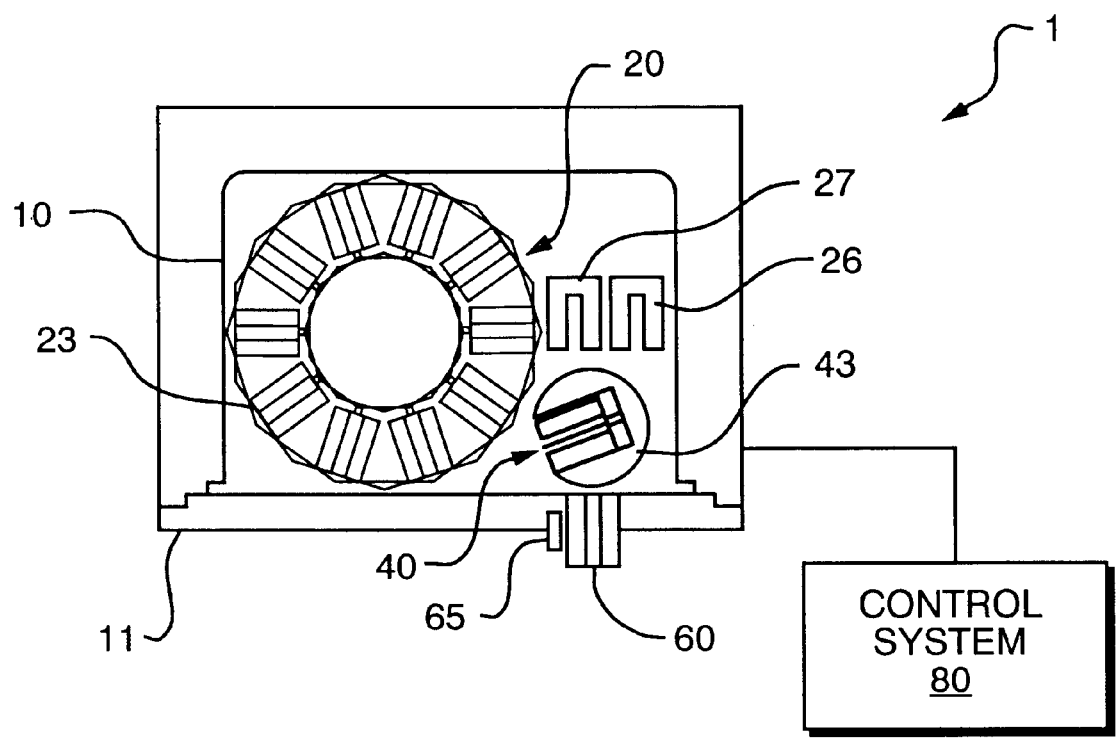
FIG. 1 shows a schematic plan view of the automated storage and retrieval apparatus.
Figure 2A:
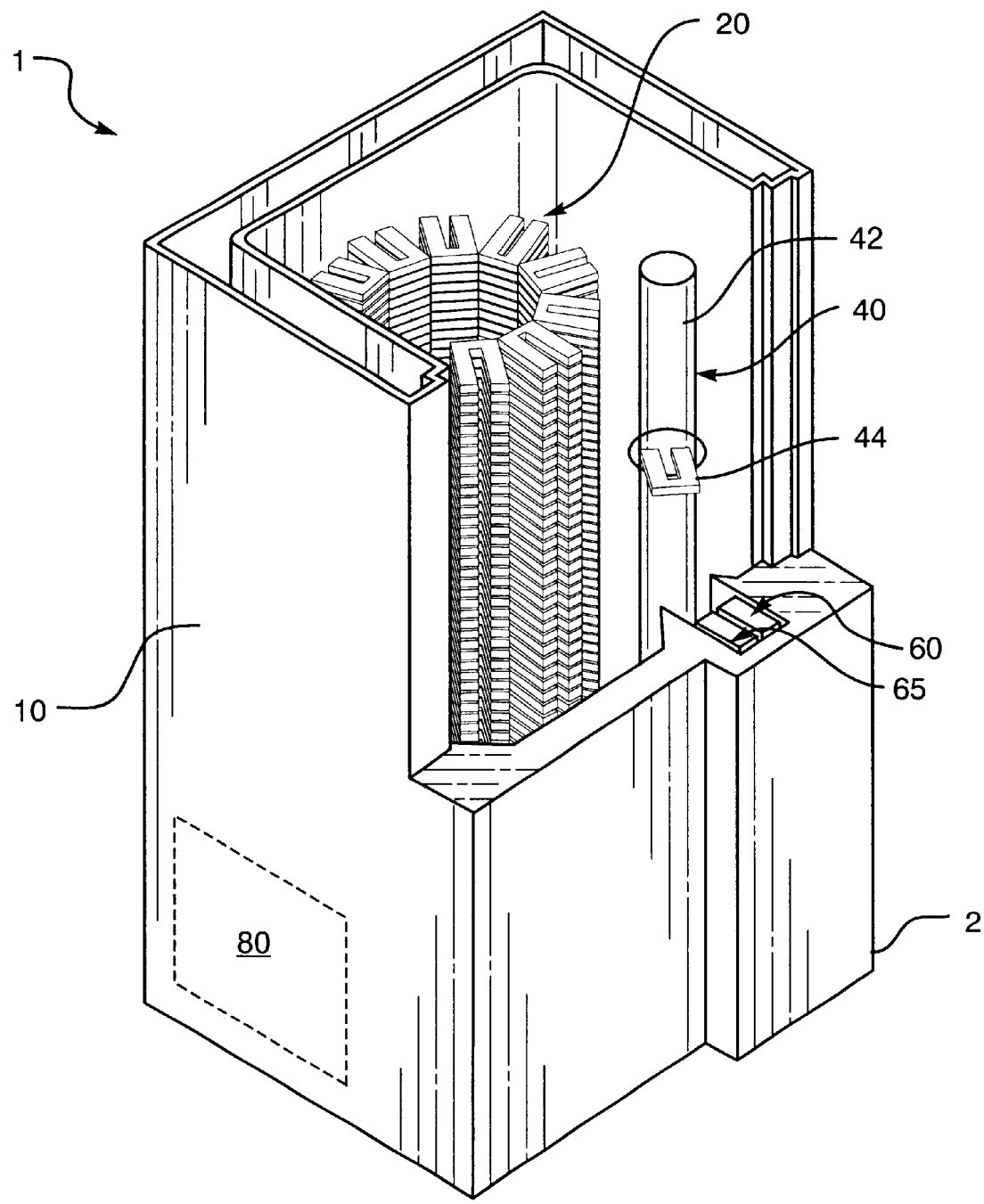
FIG. 2A shows a schematic perspective view of the automated storage and retrieval apparatus.

Turning now to the drawings, the present invention is schematically shown in the plan view of FIG. 1 and perspective view of FIG. 2A, which includes an automated storage and retrieval apparatus 1 having one or more storage carousels 20 disposed in a freezer compartment 10, with one or more optional stationary racks 26, 27, an interchange mechanism 40, and a climate controlled chamber 60 that is generally disposed on a wall 11 of the freezer compartment 10 or associated housing 2. A central control system 80 is coupled to the storage carousel 20, interchange mechanism 40, and climate controlled chamber 60 for controlling their operations. Generally, the control system 80 controls the operation of the apparatus so that the containers can be loaded from the exterior into the climate-controlled chamber 60 for retrieval by the interchange mechanism 40 for insertion onto the carousel 20 in the freezer compartment 10. Stored containers subsequently can be retrieved from the carousel 20 by the interchange mechanism 40 and available to be taken away to the exterior through the climate controlled chamber 60.

Figure 2B:
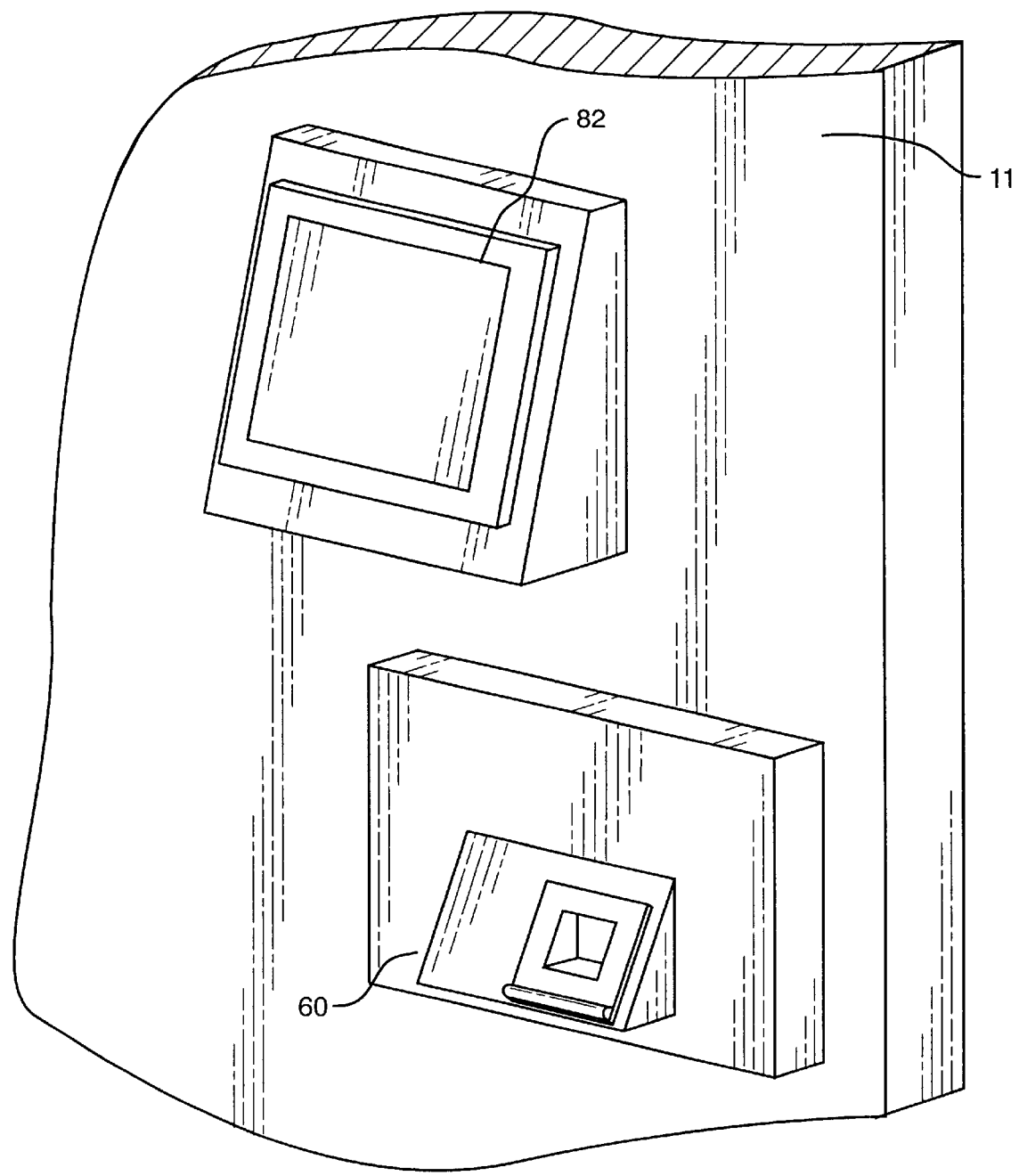
FIG. 2B shows a perspective partial view of the door or wall of a compartment and/or housing.

FIG. 2B shows a perspective partial view of the wall 11 of the compartment and/or door of the housing. Mounted on the wall 11 are the climate-controlled chamber 60 and a touch screen interface 82. As will be discussed later, it is envisioned that a control system and computer system can be accessed directly by using the touch screen interface 82 and/or remotely by a stand-alone personal computer or with a local area network (LAN).

Figure 3:
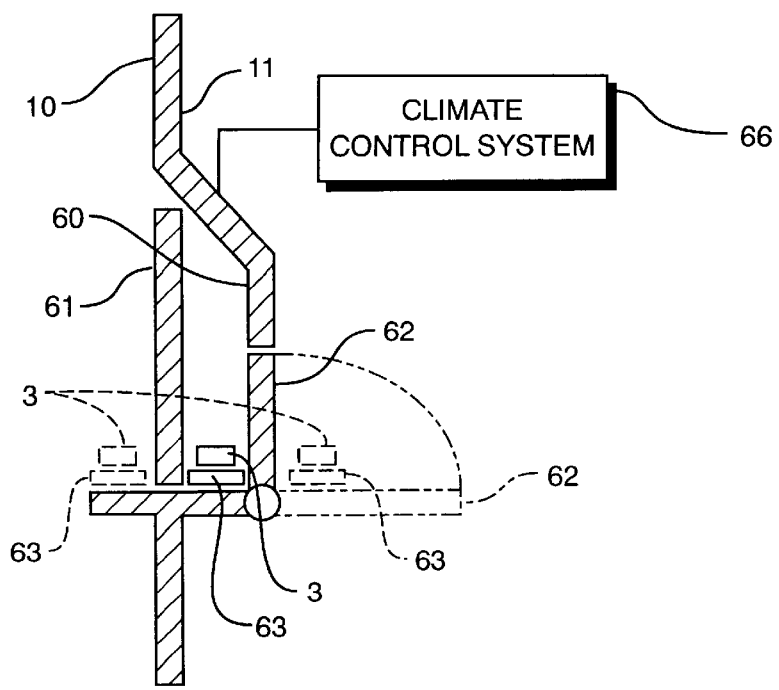
FIG. 3 shows a schematic cross-sectional view of the climate controlled chamber with the exterior door in open and closed positions.
Figure 4A:
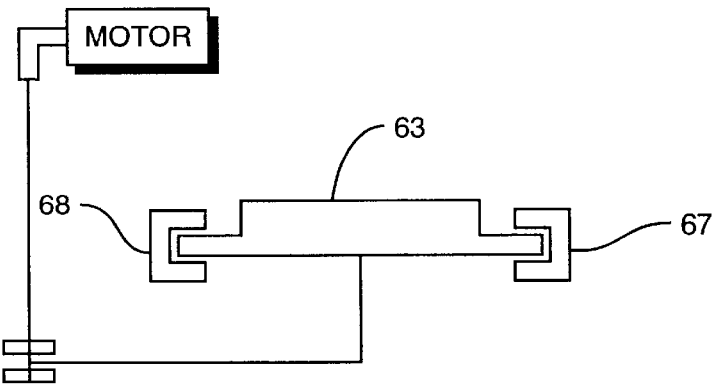
FIGS. 4A and 4B show a schematic frontal view and plan view, respectively, of the related translation mechanisms of the climate controlled chamber.
Figure 4B:
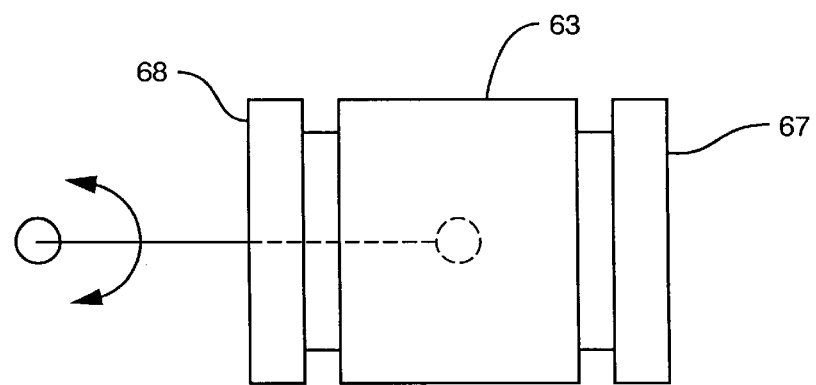
Figure 5A:
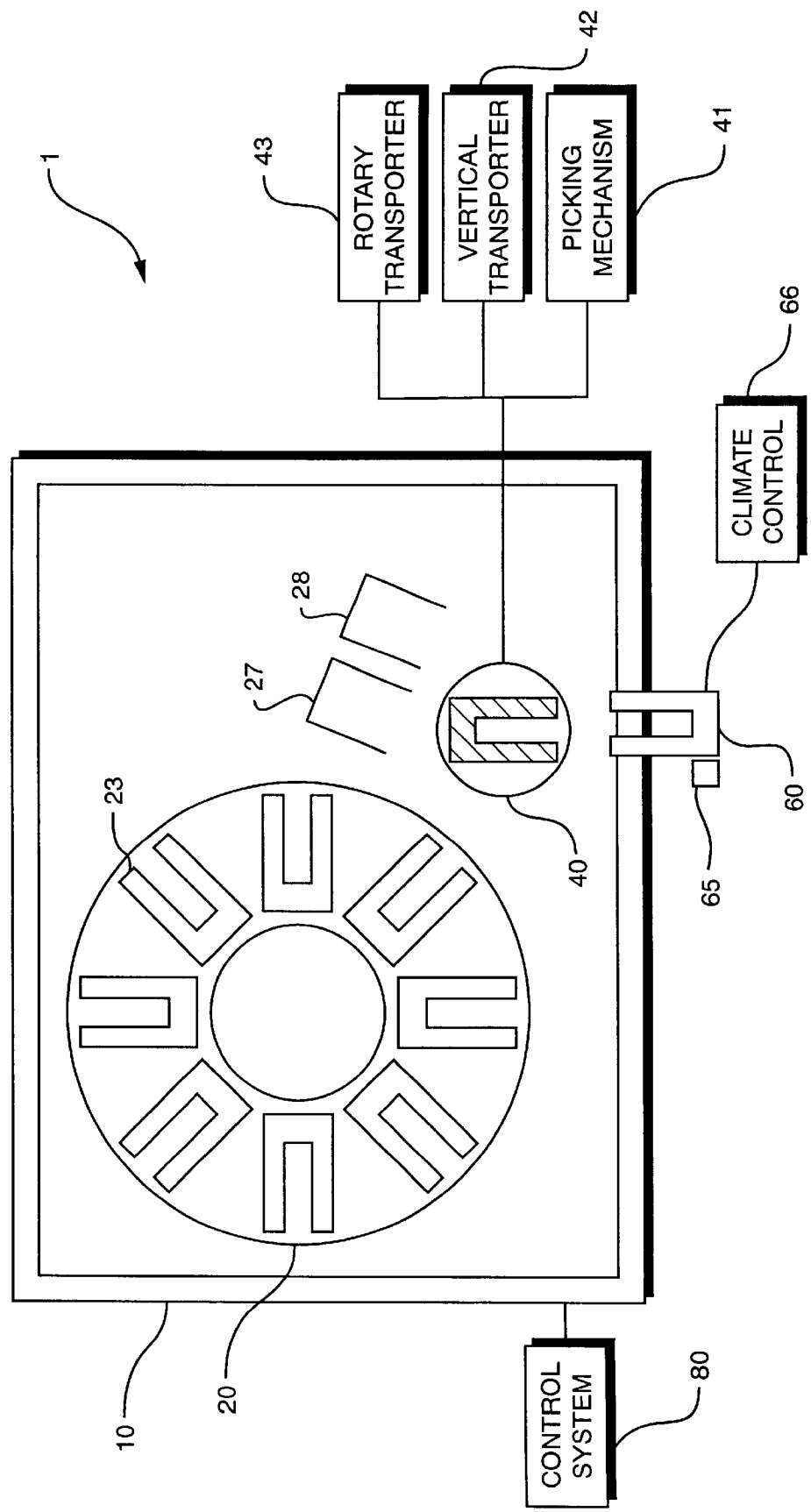
FIGS. 5A–5D show a schematic representation of select positions of the rotational alignment of the interchange mechanism.
Figure 5B:
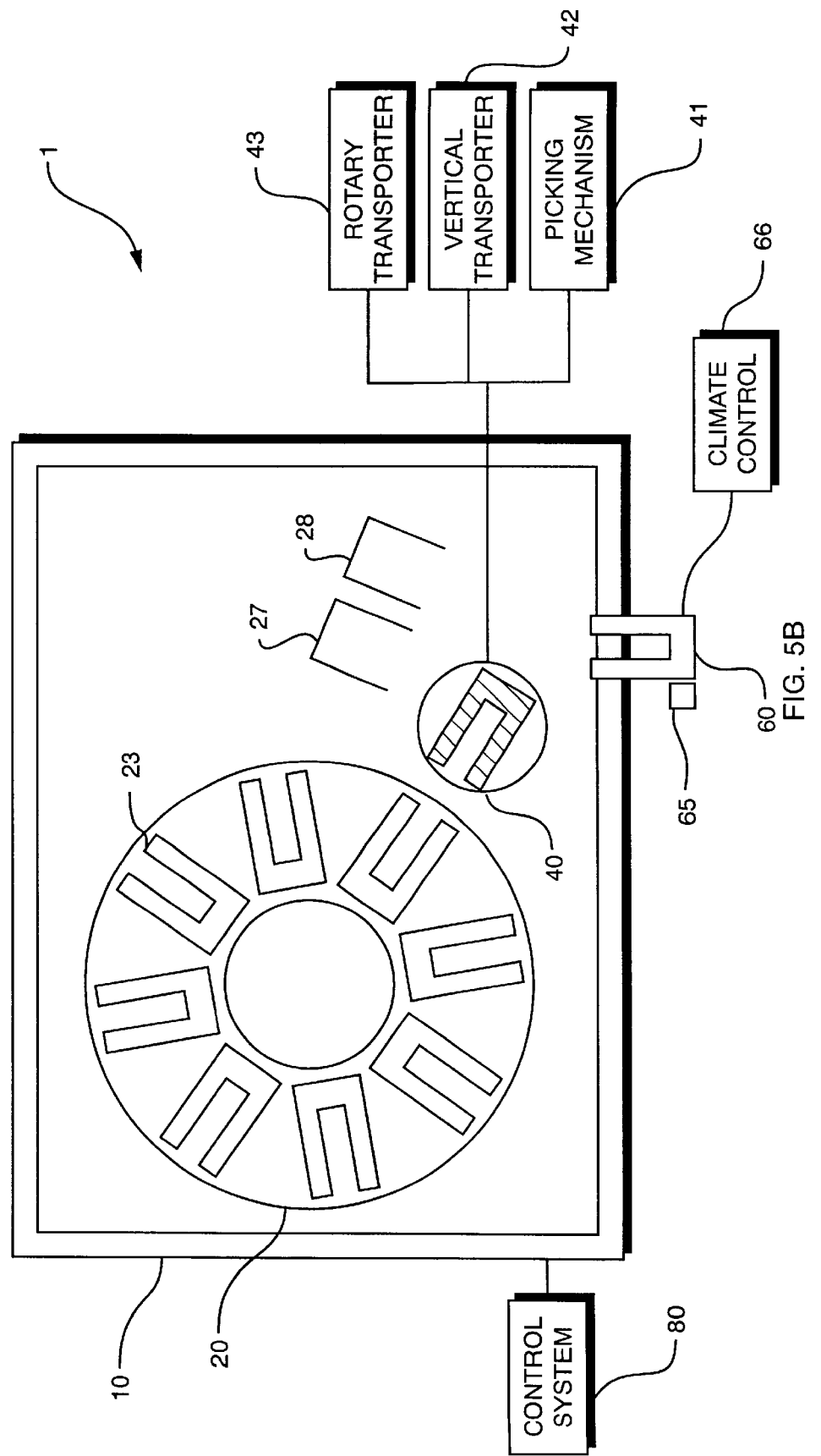
Figure 5C:
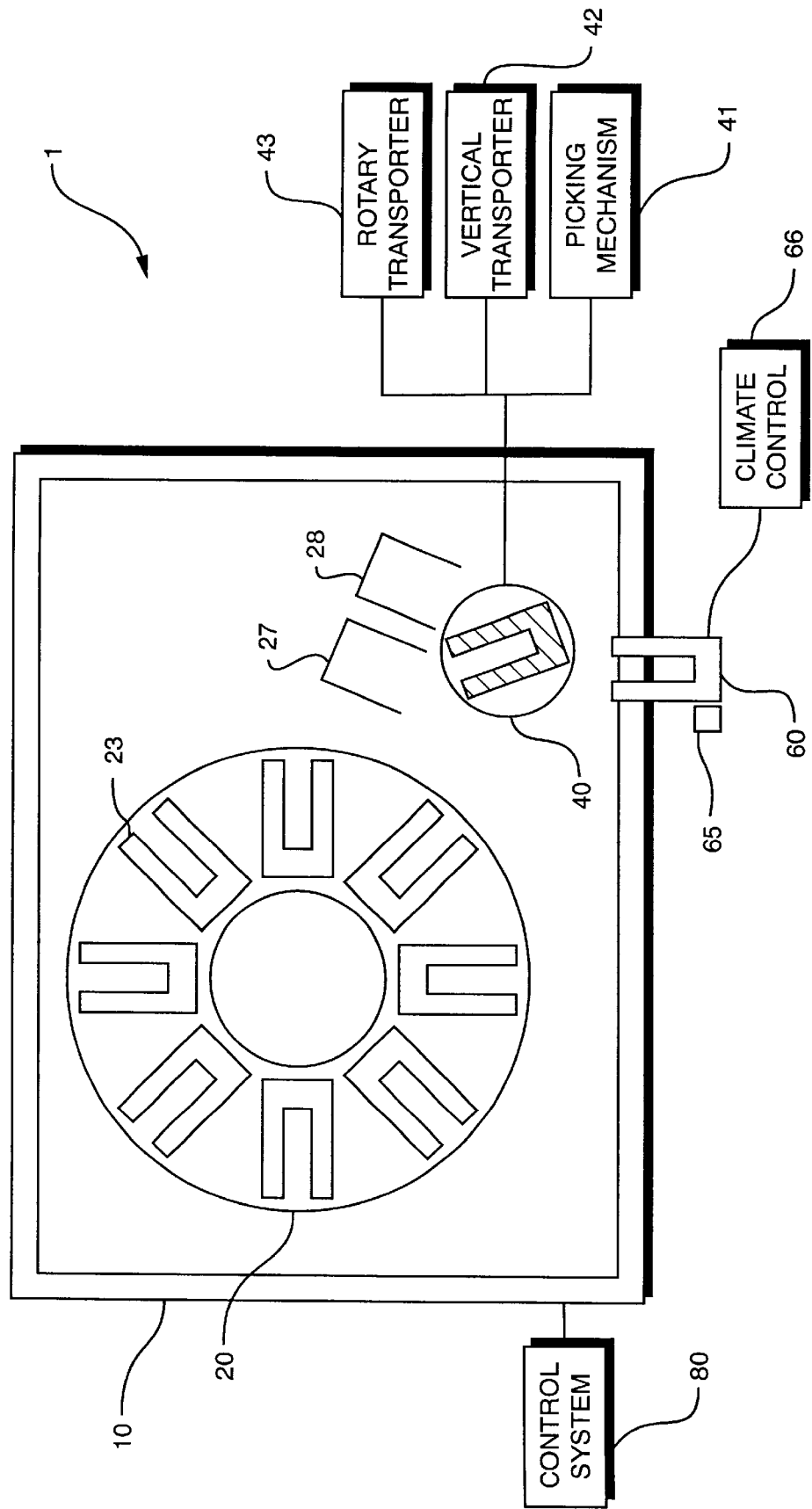
Figure 5D:
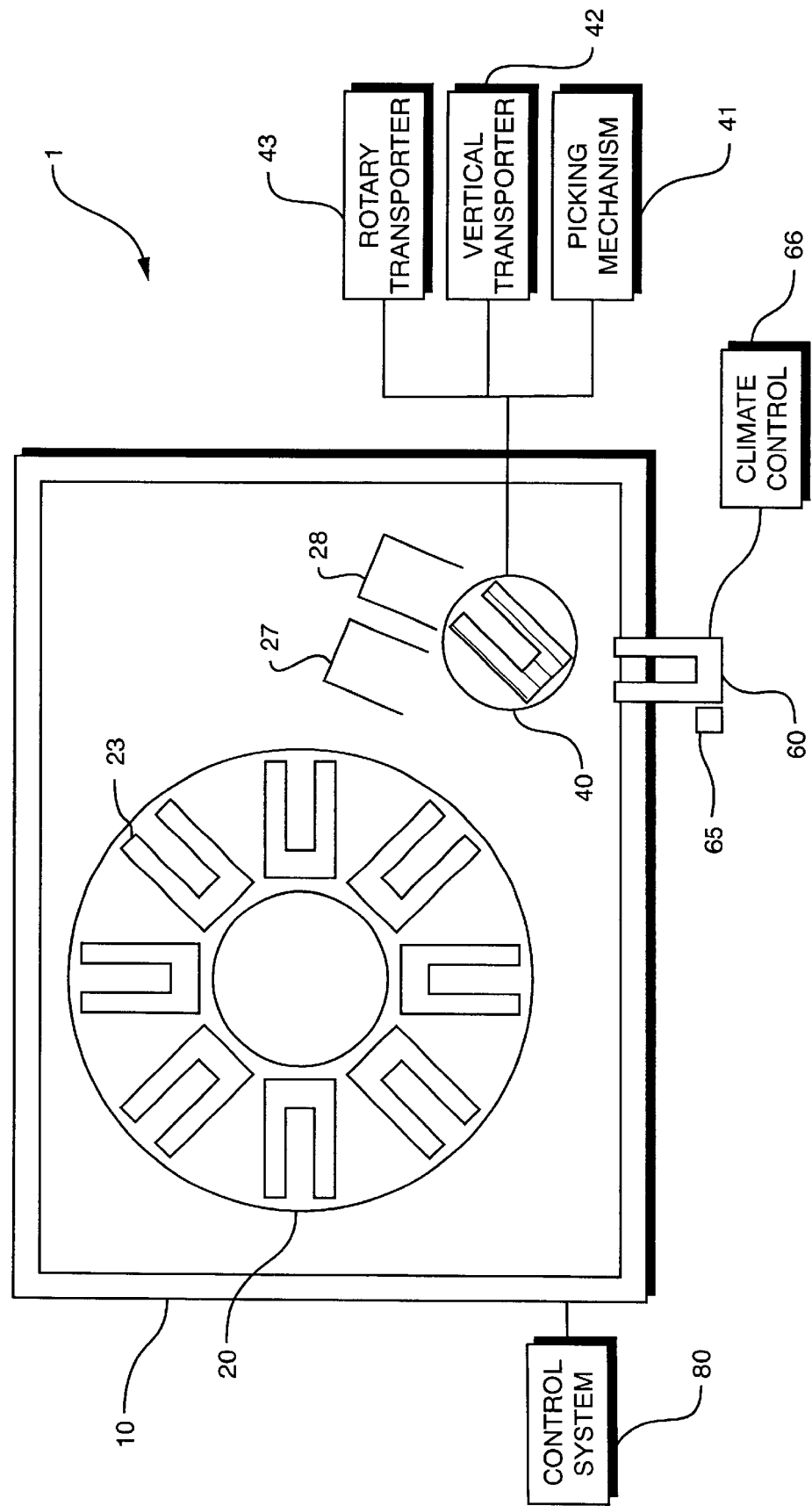

Next, details of the climate controlled chamber 60 will be provided, as best shown in FIGS. 3 and 4A–4B. A particularly desirable feature is that the climate-controlled chamber 60 prevents ambient, humid air from entering the interior of freezer compartment 10 during storage container insertion and retrieval. The Chamber 60 has an interior door 61 to allow communication between freezer compartment 10 and chamber 60, and an exterior door 62 to allow communication between the exterior environment (or adjacent area) and chamber 60. The chamber 60 has a climate control system 66 that provides an air purging capability to cool and dehumidify the air in the chamber 60 before interior door 61 is opened. A scanning reader device 65, preferably a barcode reader, is situated in the chamber 60 to identify storage containers as they are inserted into and retrieved from chamber 60. Information relative to the storage containers is transmitted from reader device 65 to central and/or remote processor.

Still referring to FIGS. 3 and 4A–4B, the storage containers 3 are carried by a transport tray 63 that is slidably mounted on two channels 67, 68. The transport tray 63 can transport the container 3 to the exterior as the exterior door 62 is open, as indicated by the dashed lines. Alternatively, the transport tray 63 can transport the container 3 to the interior of the freezer compartment 10 as the interior door 61 is open, as indicated by the dotted lines. In one embodiment, the interior door 61 may slide open and close on a track (not shown). A climate control system 66 is in communication with the chamber 60 that dehumidifies and cools the chamber 60 while the container is isolated therein, i.e., both exterior and interior doors are closed. The climate control system 66 includes a dry gas or dry air purge (i.e., nitrogen, carbon dioxide, or the like), that rapidly reduces ambient humidity to any desired level, e.g., less than about 25% relative humidity (RH) and as low as about 1% RH. In fact, any compressed gas from which moisture has been removed will reduce the humidity in the airlock, and will cool the airlock by adiabatic expansion to about $-10°$ C. to about $0°$ C., or as desired.

A preferred embodiments of the present invention automated storage and retrieval apparatus, and related method thereof, operate at an ultra low temperature from about $-50°$ C. to about $-90°$ C. It should be understood that the apparatus may operate in a range of $-50°$ C. up to ambient temperature or greater. The normal design operating temperature of the freezer compartment of the present invention is about $-80°$ C. It should be noted that the present invention is contemplated to operate at conditions colder than ultra low temperatures in the range of about $-140°$ C. to about $-90°$ C. Conveniently, if the freezer fails for whatever reason—maintenance or scheduled outage—then liquid carbon dioxide can be pumped into the system and keep it at approximately $-78°$ C. Thus, the ultra low freezer-set point of the apparatus can be backed up by installing a cylinder of liquid carbon dioxide.

One skilled in the art would appreciate that various types and substitutes for interior and exterior chamber doors can be used. Moreover, a single door can be utilized which can rotate between interior and exterior sides.

Figure 16A:
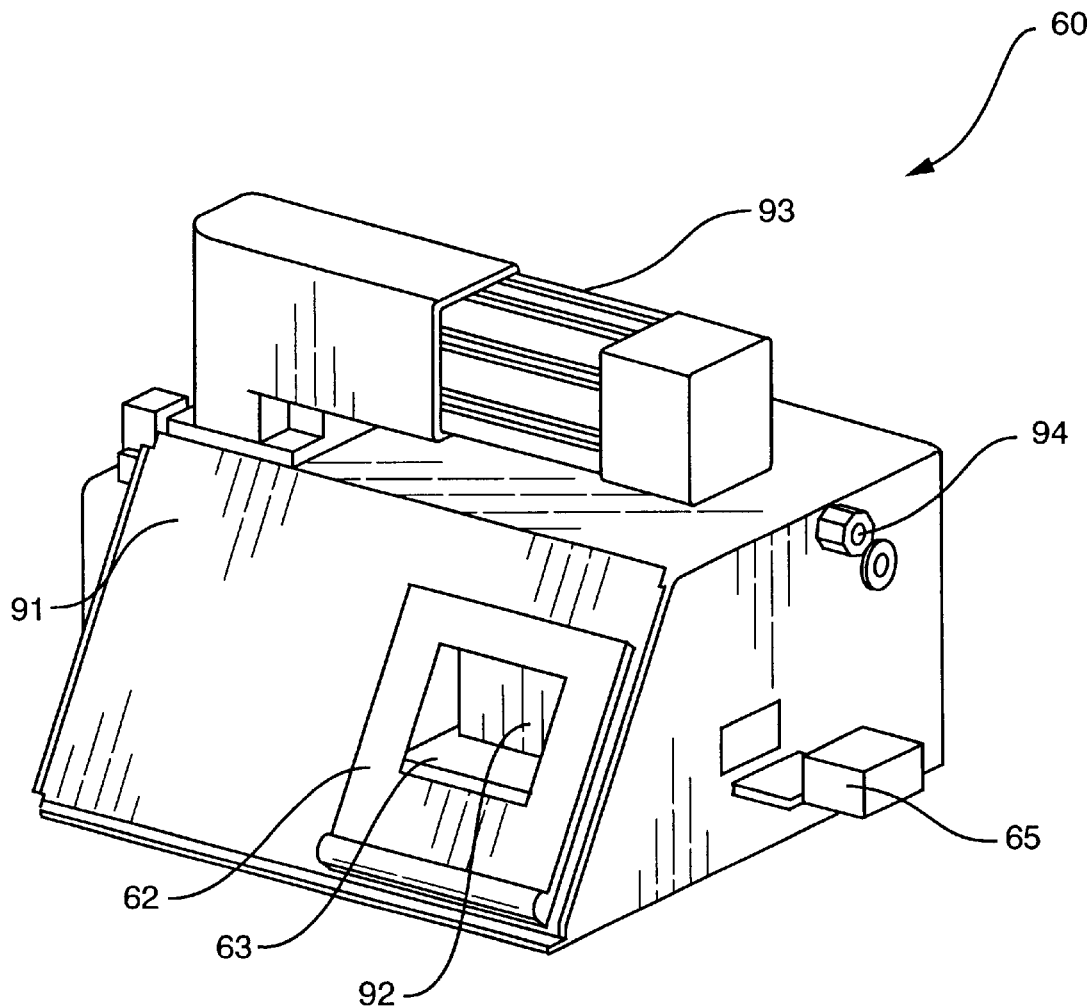
FIGS. 16A and 16B show schematic perspective front/exterior views of the housing of the climate control chamber with related components in both the closed and open position, respectively.
Figure 16B:
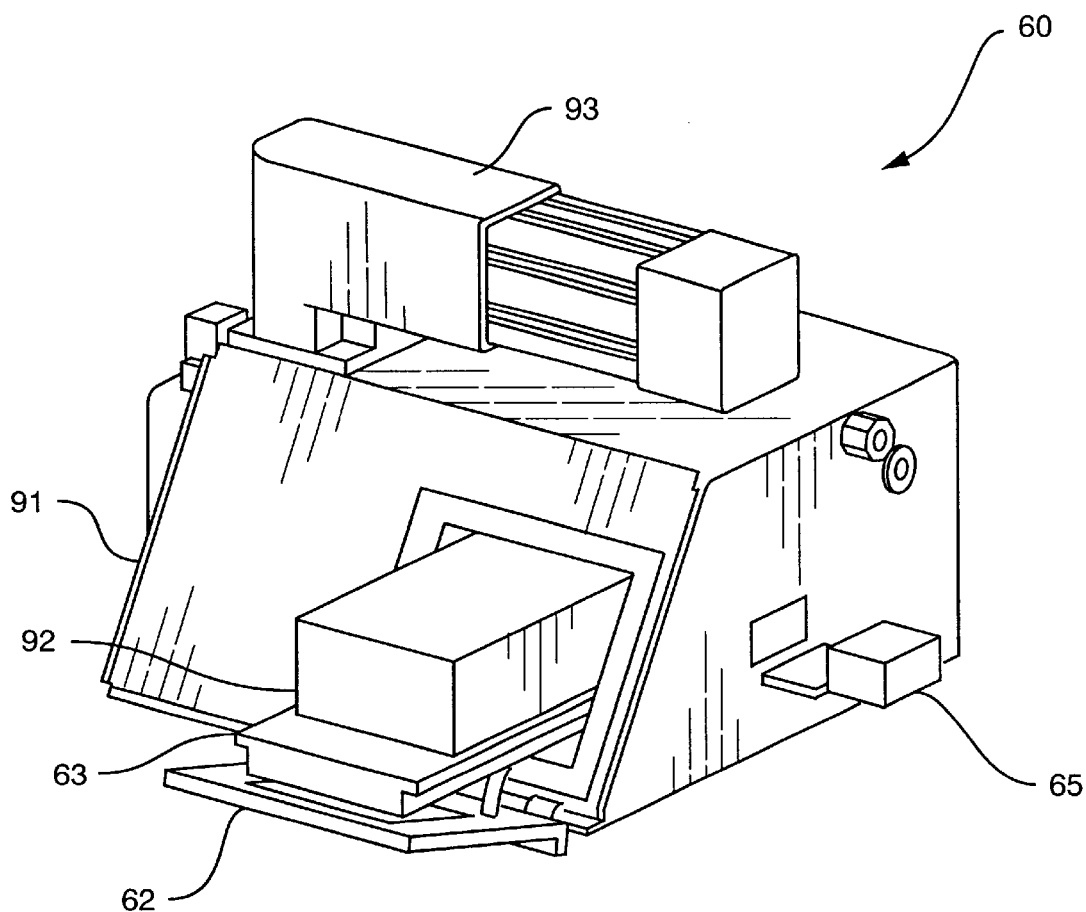

Additional details pertaining to the climate controlled chamber 60 will be provided, as best shown in the perspective views of FIGS. 16A–16B and FIGS. 17A–17B. The front/exterior view and the back/interior view of climate controlled chamber 60 are shown in FIGS. 16A–16B and FIGS. 17A–17B, respectively. Referring to front/exterior view of FIG. 16A, the chamber 60 includes a chamber housing 91 having its exterior door 62 in a closed position with a deep well micro-plate 92 placed thereon the transport tray 63. It should be appreciated that a shallow well microplate may be used, as well as any other size, type, or number of containers, which can be accommodated for storage and interchange. Also shown is a tray-motor and gear box housing 93, reading device 65, and air purge port 94. FIG. 16B shows the chamber 60 having its exterior door 62 in an open position.

Figure 17A:
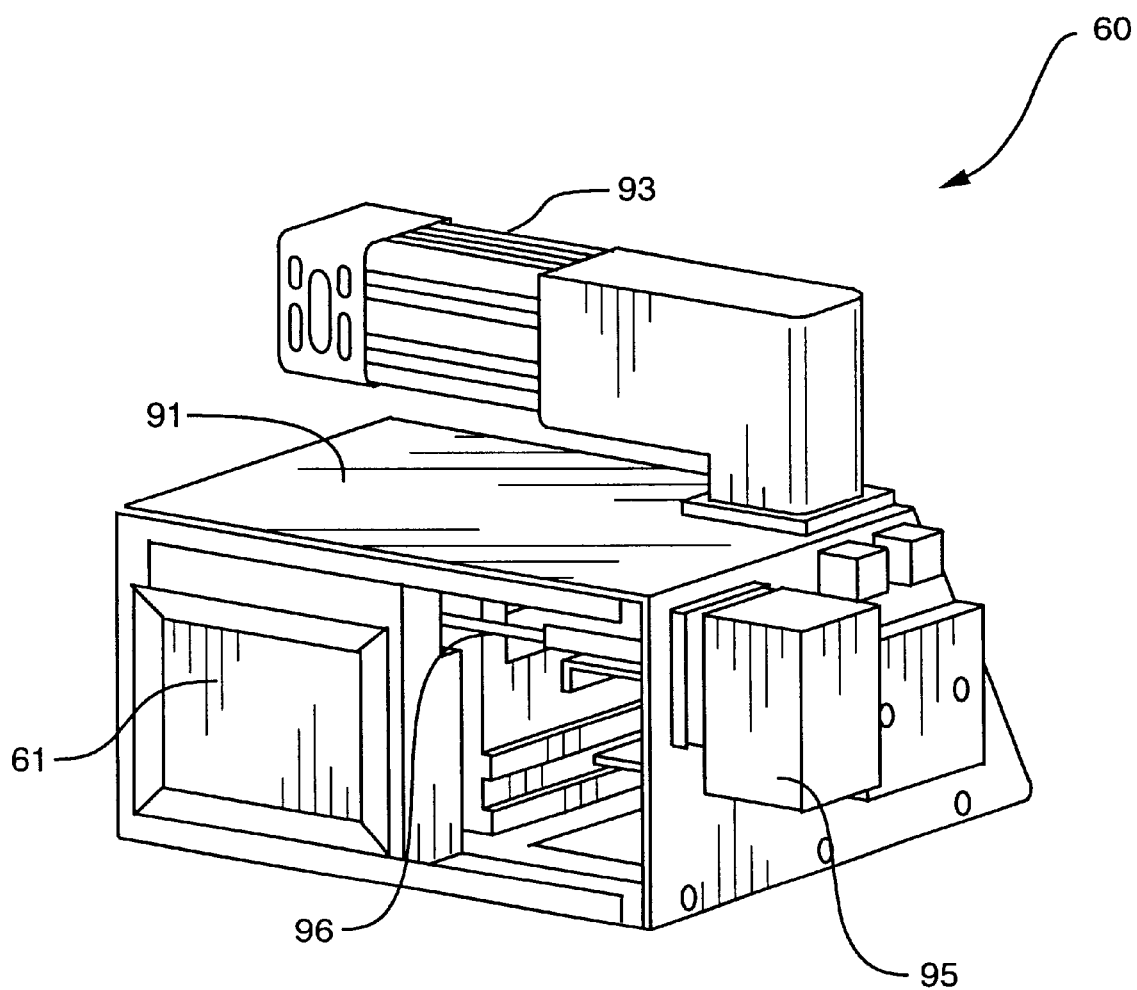
FIGS. 17A and 17B show schematic perspective back/interior views of the housing of the climate control chamber with related components in both the closed and open position, respectively.
Figure 17B:
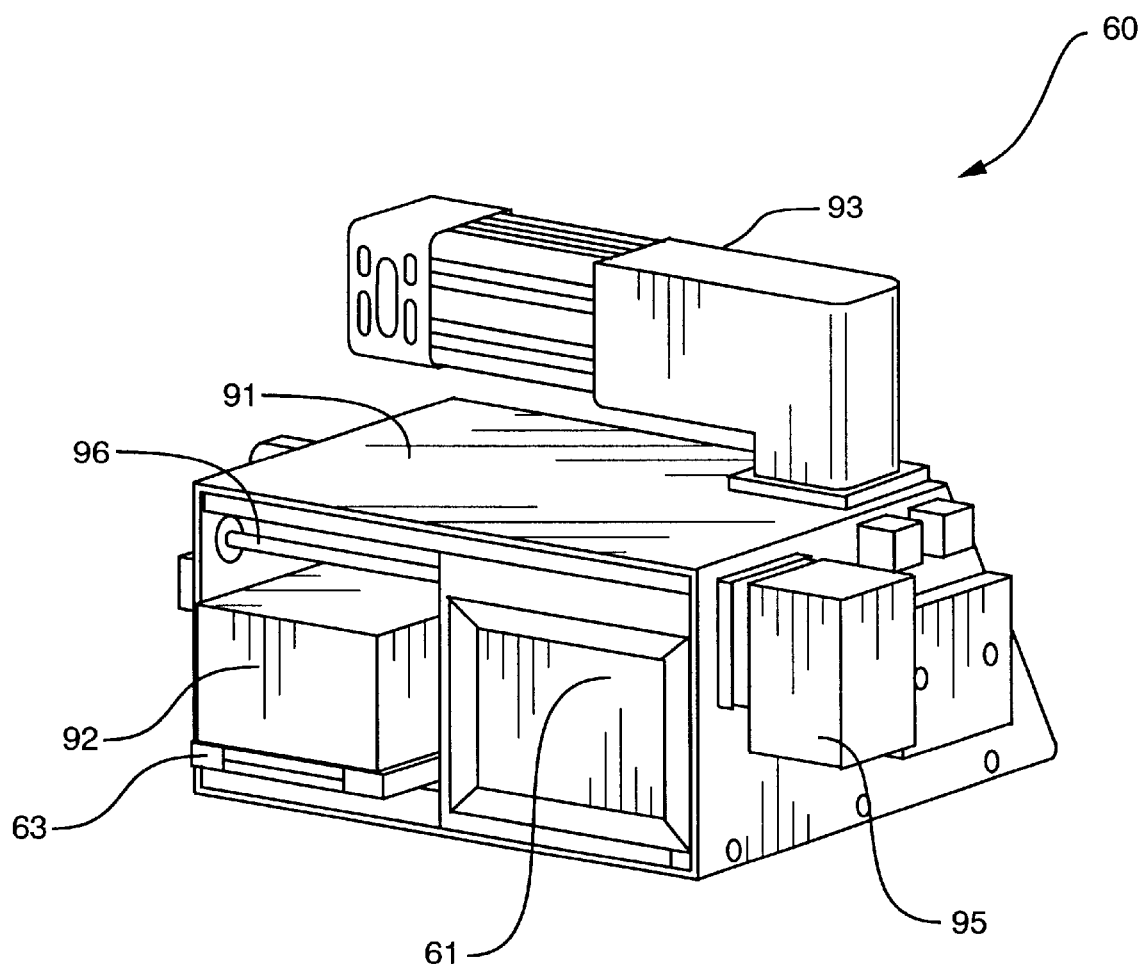

Referring to the back/interior view of FIGS. 17A–17B, there is shown the chamber 60 including an interior door-motor gear and motor housing 95 and lead screw 96, and having its interior door 61 in a closed position. FIG. 17B shows the chamber 60 having its interior door 61 in an open position with the deep well micro-plate 92 placed thereon the transport tray 63.

Additional details of the cooperation between the freezer compartment 10, carousel 20, stationary racks 26, 27, interchange mechanism 40, and climate-controlled chamber 60 are schematically shown referring to FIGS. 5A–5D. The interchange mechanism 40 is configured to interchange containers between it and the carousel 20 (See FIG. 5B), stationary storage racks 26, 27 (See FIGS. 5C–5D, respectively), and the climate-controlled compartment 60 (See FIG. 5A). Various storage means besides the disclosed carousels or stationary racks are contemplated, such storage means include the following but are not limited thereto automated stackers, and with possible additional hardware, rectangular arrays of storage nests (or any predetermined shaped carousel/rack including linear, oval, pentagonal, hexagonal, etc.). The interchange mechanism 40 requires a picking mechanism 41 for horizontally translating the interchange tray 44 for interchanging the container 3 with the carousel 20 or the climate controlled chamber 60. Various picking mechanisms include, but not limited thereto lead screws, picking devices, vacuum devices, side gripping fingers, vertical pincers, and conveyors. The interchange mechanism 40 further comprises a vertical transporter 42 configured to allow the interchange mechanism 40 to be translated vertically over a plurality of discrete heights. Various vertical transporters include, but not limited thereto lead screws, chain drives, and conveyors. Further yet, the interchange mechanism 40 comprises a rotary transporter 43 that is configured to rotate the interchange mechanism 60 to a plurality of discrete circumferential positions. Various rotary mechanisms include, but not limited thereto lead screws, pivot devices, gear drives, belt or chain drives, pneumatic or hydraulic devices, and conveyors.

With regards to control operations, the present invention automation and robotic motions described herein are provided in part by the control system 80 and processor 81. It should be noted that the following exemplary sequences of operations may be varied, partially omitted, overlapped to reduce the total elapsed time of operation, or reordered in an alternative sequence.

Figure 6A:
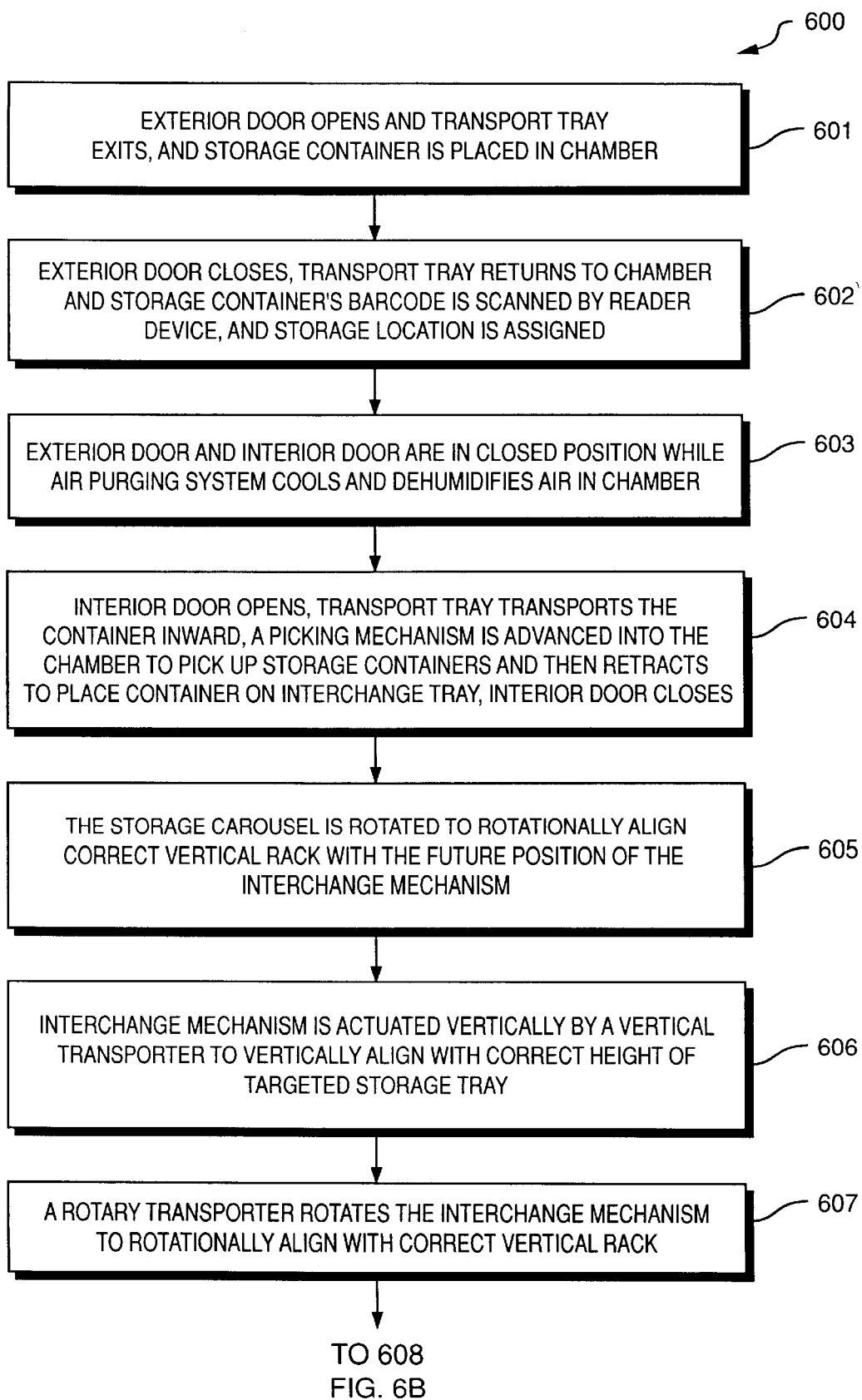
FIGS. 6A and 6B comprise a flow chart illustrating the operation for depositing and storing a storage container or the like in the automated storage and retrieval apparatus.
Figure 6B:
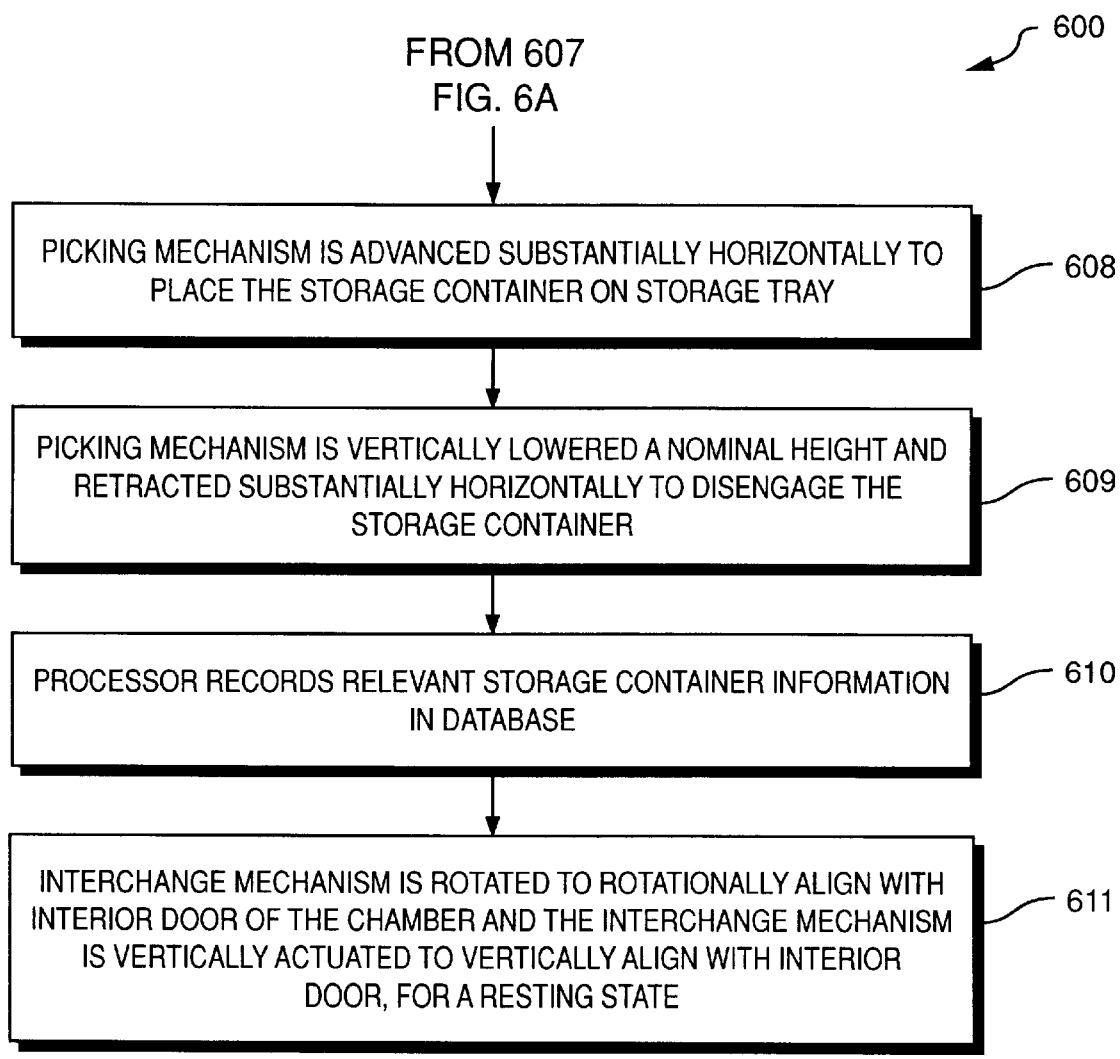

Operation for depositing 600 a storage container is provided in the flowchart of FIGS. 6A–6B. In a first step, 601, the exterior door 62 opens and transport tray 63 exits, and storage container 3 is placed in chamber 60. In step 602, the exterior door 62 closes, transport tray 63 returns to chamber 60 and storage container's barcode is scanned by reader device 65, and storage location is assigned. In step 603, exterior door 60 and interior door 61 are in closed position while air purging system 66 cools and dehumidifies air in the chamber 60. In step 604, the interior door 61 opens, the transport tray 63 transports the container 3 inward, a picking mechanism 43 is advanced into the chamber 60 to pick up the storage containers and then retracts to place the container 3 on interchange tray 44, and the interior door closes. In step 605, the storage carousel 20 is rotated to rotationally align the correct vertical rack 23 with the future position of the interchange mechanism 40. In step 606, the interchange mechanism 40 is actuated vertically by a vertical transporter 42 to vertically align with correct height of targeted storage tray 28. In step 607, a rotary transporter 43 rotates the interchange mechanism 40 to rotationally align with correct vertical rack 23. In step 608, the picking mechanism 43 is advanced substantially horizontally to place the storage container 3 on storage tray 28. In step 609, the picking mechanism 43 is vertically lowered a desired nominal distance, e.g., approximately ⅛-inch, and retracted substantially horizontally to disengage the storage container 3. In step 610, the processor records relevant storage container information in the database. In step 611, provided no other activity is required at the storage carousel 20 (or at any stationary storage rack 26, 27) the interchange mechanism 40 is rotated to rotationally align with interior door 61 of the chamber 60 and the interchange mechanism 60 is vertically actuated to vertically align with interior door 61, for a resting state. It should be noted that a similar process and aspect applies to the stationary racks 26, 27, except that the racks do not rotate.

Figure 7A:
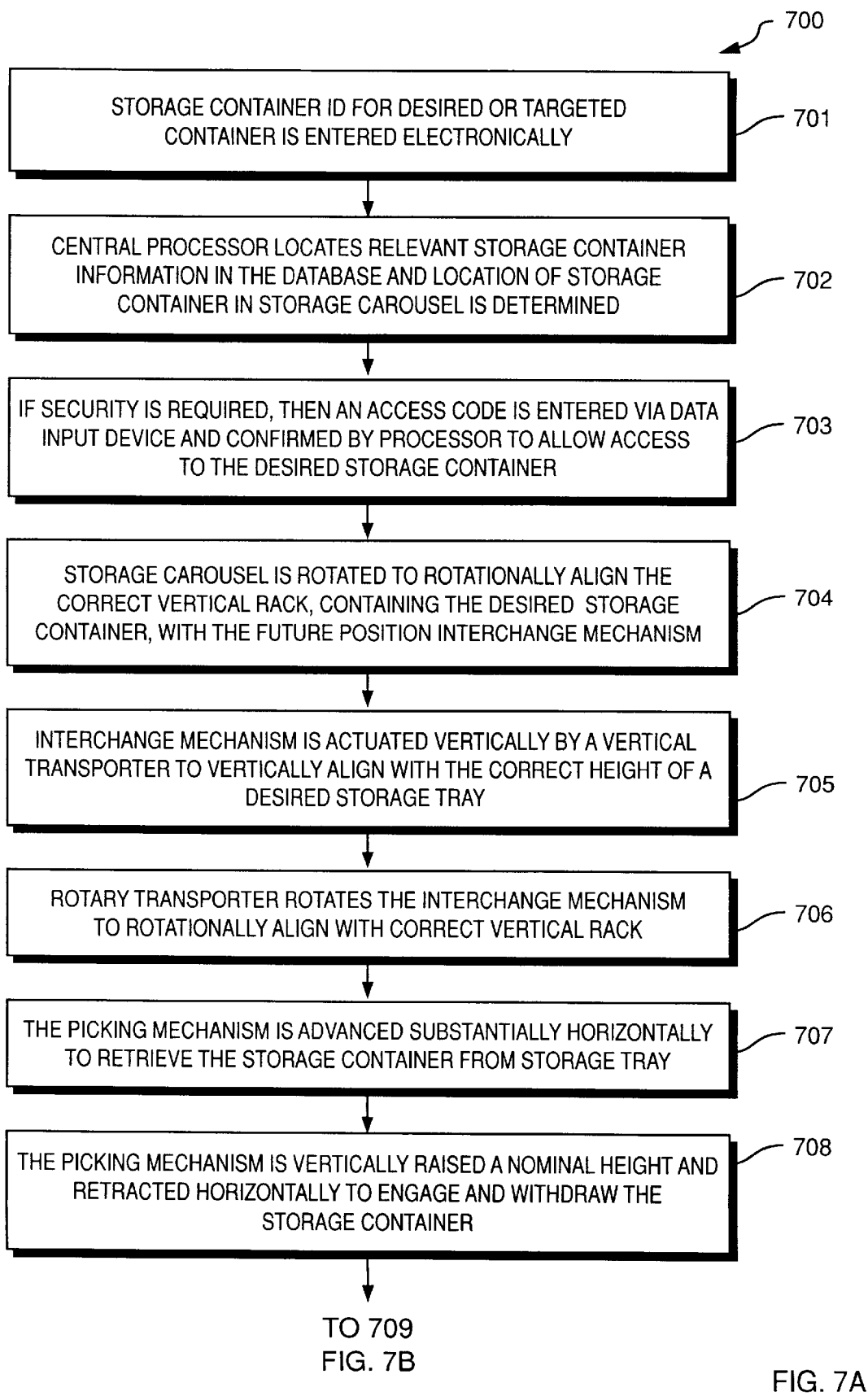
FIGS. 7A and 7B comprise a flow chart illustrating the operation for retrieving the targeted or desired storage container or the like in the automated storage and retrieval apparatus.
Figure 7B:
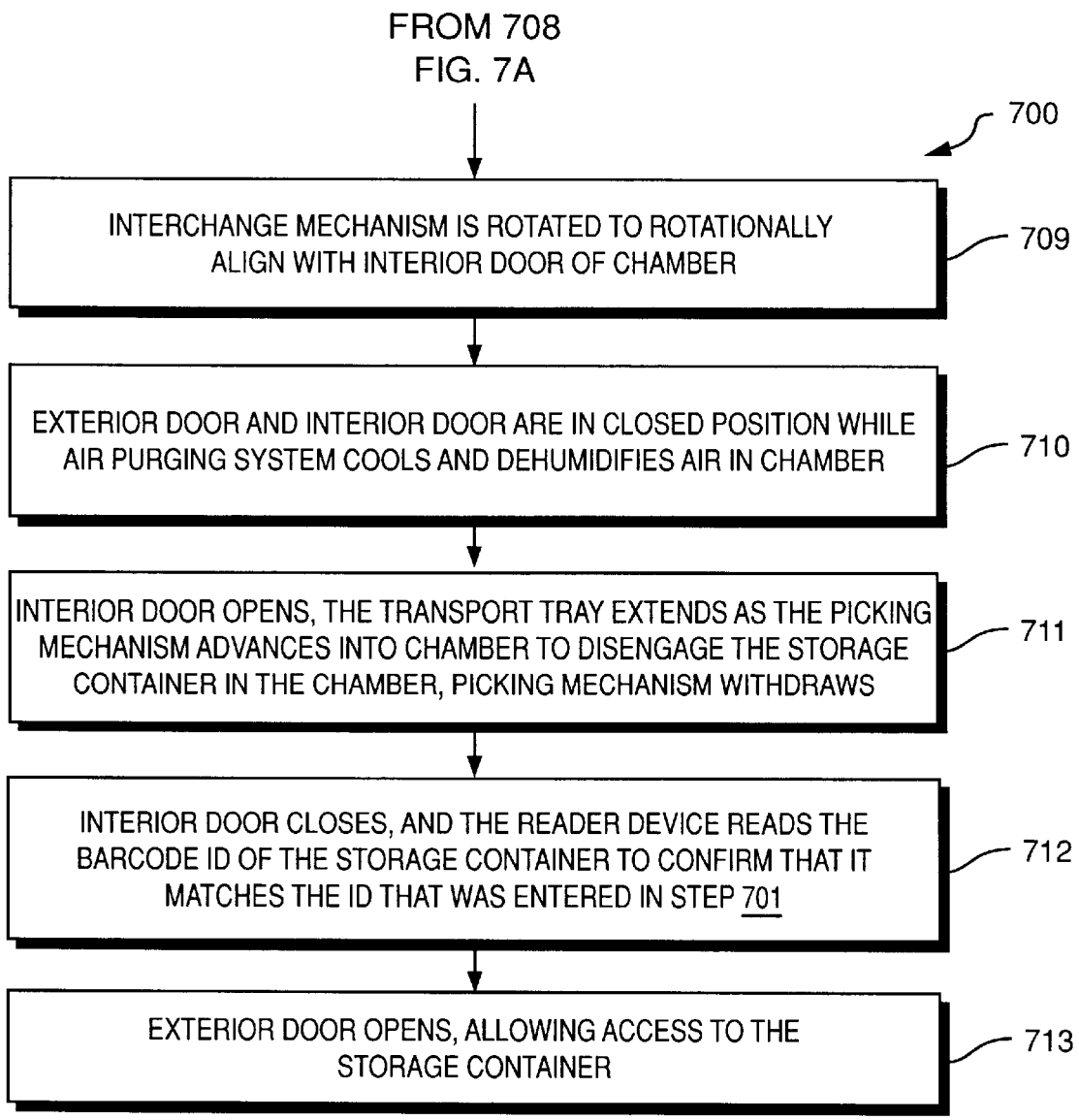

Next, the operation for retrieving 700 the desired or targeted containers 3 from the storage trays 28, is.provided in the flowchart of FIGS. 7A–7B. In a first step 701, a storage container identification (ID) for a desired or targeted container is entered electronically or via data input device such a display panel integral with the apparatus housing or a remote there from, both of which being operatively connected to the control system 80. In step 702, a central processor 81 locates relevant storage container information in the database and location of storage container in storage carousel 20 (or stationary storage racks) is determined. Optionally, step 703 , if security is required, then an access code is entered via data input device such a display panel integral with the apparatus housing or a remote processor, and confirmed by central processor 81 to allow access to the desired storage container 3. In step 704, the storage carousel 20 is rotated to rotationally align the correct vertical rack 23, containing the desired storage container 3, with the future position of the interchange mechanism 40. In step 705, the interchange mechanism 40 is actuated vertically by a vertical transporter 42 to vertically align with the correct height of a desired storage tray 28. In step 706, the rotary transporter 43 rotates the interchange mechanism 40 to rotationally align with correct vertical rack 23. In step 707, the picking mechanism 43 is advanced substantially horizontally to retrieve the storage container 3 from storage tray 28. In step 708, the picking mechanism 43 is vertically raised a desired nominal distance, e.g., approximately ⅛-inch, and retracted horizontally to engage and withdraw the storage container 3. In step 709, the interchange mechanism 40 is rotated to rotationally align with interior door 61 of chamber 60. In step 710, the exterior door 62 and interior door 61 are in closed positions while air purging system 66 cools and dehumidifies air in chamber 60. In step 711, the interior door 61 opens, the transport tray 63 extends as the picking mechanism 43, advancing into chamber 60 to disengage the storage container in the chamber 60. In step 712, the picking mechanism withdraws into the freezer compartment and the interior door 61 closes, and the reader device 65 reads the barcode ID of the storage container to confirm that it matches the ID that was entered in step 701 of the present invention retrieval process. In step 713, the exterior door 62 opens, allowing access to the storage container 3. It should be noted that a similar process and aspect applies to the stationary racks 26, 27, except that the racks do not rotate.

Figure 8:
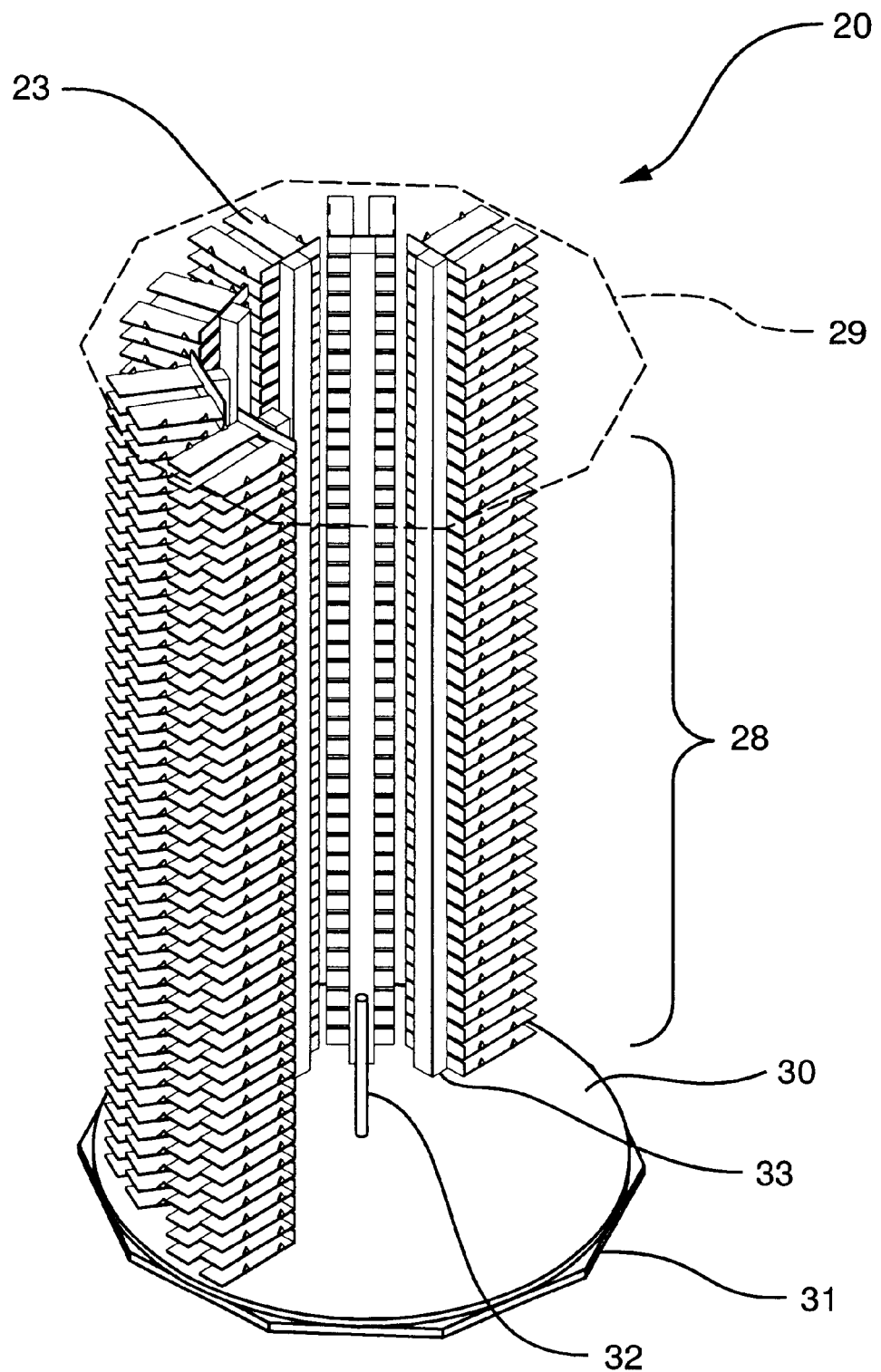
FIG. 8 shows a schematic perspective view of the storage carousel of the automated storage and retrieval apparatus.
Figure 9:
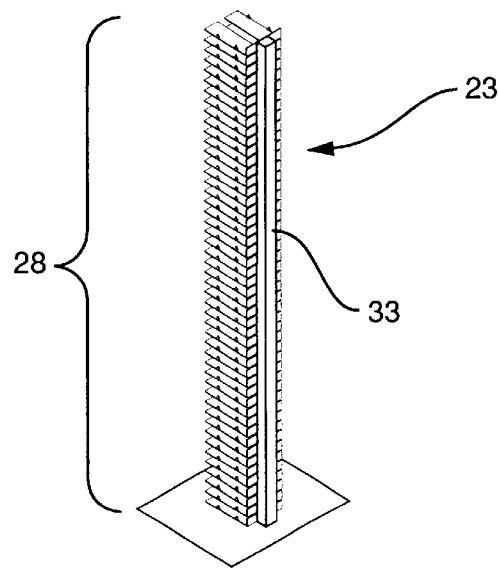
FIG. 9 shows a perspective view of an individual vertical rack from the carousel of FIG. 8, comprised of a plurality of storage trays.

Next, details pertaining to the storage carousel 20 will be discussed, as schematically shown in FIGS. 8–9. The perspective view as shown in FIG. 8 includes a carousel 20 having some racks 23 omitted for illustration purposes. The carousel 20 comprises an annular ring of vertical racks 23 arranged circumferentially between an upper horizontal plate 29 (shown in dashed lines) and a lower horizontal plate 30. The carousel may be various sizes, dimensions, and shapes, including linear, rectangular, pentagonal, and hexagonal or the like. A base plate 31, acts as a bearing brace to the support storage carousel 20 while allowing rotation of carousel 20 about the vertical axis. Rotation of carousel 20 is actuated by a motor driveshaft 32, which runs through lower horizontal plate 30 and base plate 31 to communicate with a motor (not shown). The motor is preferably mounted beneath the floor of freezer compartment 10, where the refrigeration equipment is housed, and where the motor is not exposed to the ultra-cold temperatures of freezer compartment 10. Storage carousel 20 may rest on a ball bearing system to provide reduced friction at ultra-cold temperatures. The self-lubricating bearing system, e.g., graphite ceramic, may be used as well as other types known to those skilled in the art. Vertical racks 23 are mounted to upper horizontal plate 29 and lower horizontal plate 30 with right-angle braces or the like. The vertical racks 23 comprise a vertical support 33 and a plurality of adjustable storage trays 28 to hold a plurality of storage containers 3, which could be of standard or varying size.

FIG. 9 is a perspective view of an individual vertical rack 23, comprised of a plurality of storage trays 28.

Figure 10A:
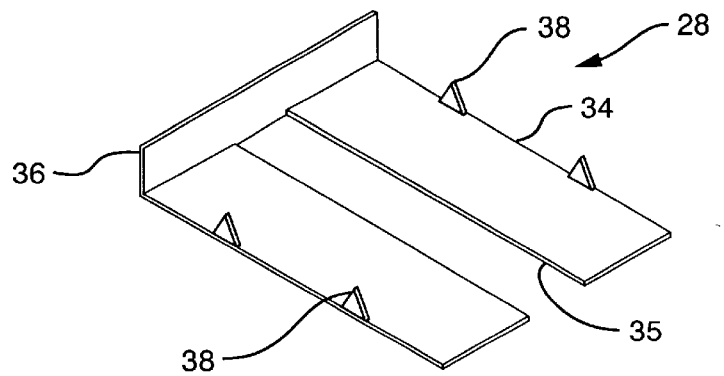
FIGS. 10A and 10B show a schematic perspective view of the storage trays and their related cooperation with the vertical supports of the carousel.
Figure 10B:
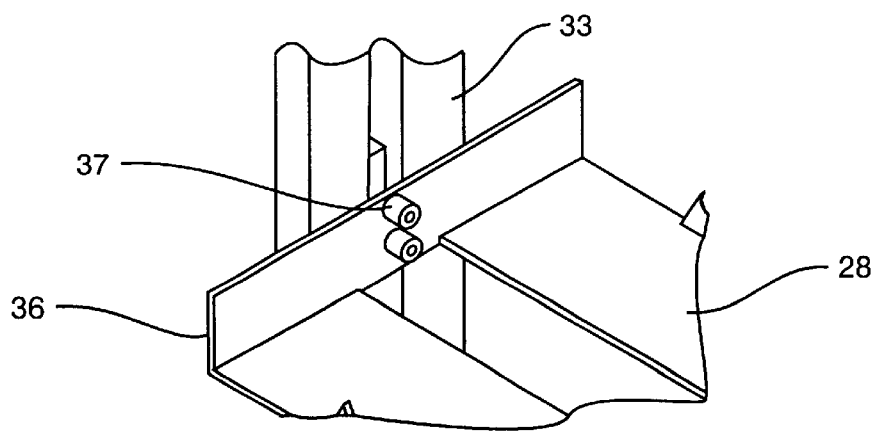

Next, details pertaining to the storage trays 28 and cooperation with the vertical support 33 of the carousel 20 will be discussed, as best shown in FIGS. 10A–10B. Storage trays 28 have a flat, horizontally oriented support surface 34 with an open center 35 to allow the interchange mechanism 40 to engage the storage containers 3 either for placement onto storage tray 28 or for retrieval from storage tray 28. The storage trays 28 have a flat vertically oriented attachment surface 36 positioned at a right angle to the proximal edge of storage trays 28, which allows connection of storage trays 28 to vertical support 33 of the vertical racks 23 by an attachment assembly 37 (partially shown). Other configurations of the attachment assembly 37 are contemplated according to the type of interactions between the various components and subsystems. The distal edge of storage trays 28 is open and outward facing to allow access to the storage containers. Other configurations of the storage trays 28 are contemplated according to the type of interactions between the various components and subsystems. Vertically oriented raised guides 38 are situated on lateral edges of storage trays 28 to prevent storage containers from becoming misaligned on storage trays 28. The raised guides 38 can be stamped out of the surface of storage trays 28, or other suitable means known to those skilled in the art.

Figure 11A:
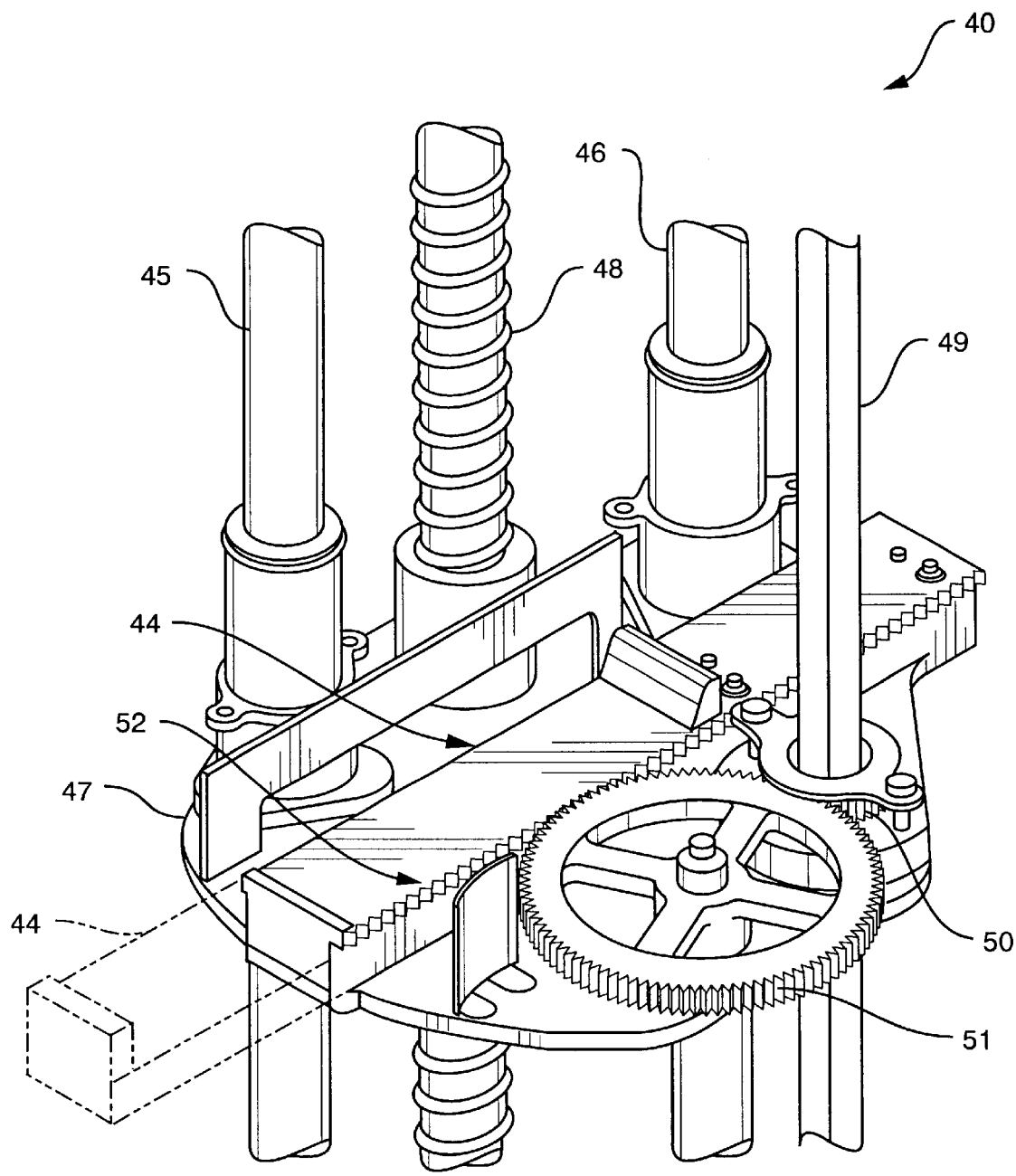
FIGS. 11A and 11B are schematic perspective views of the interchange mechanism and related components.
Figure 11B:
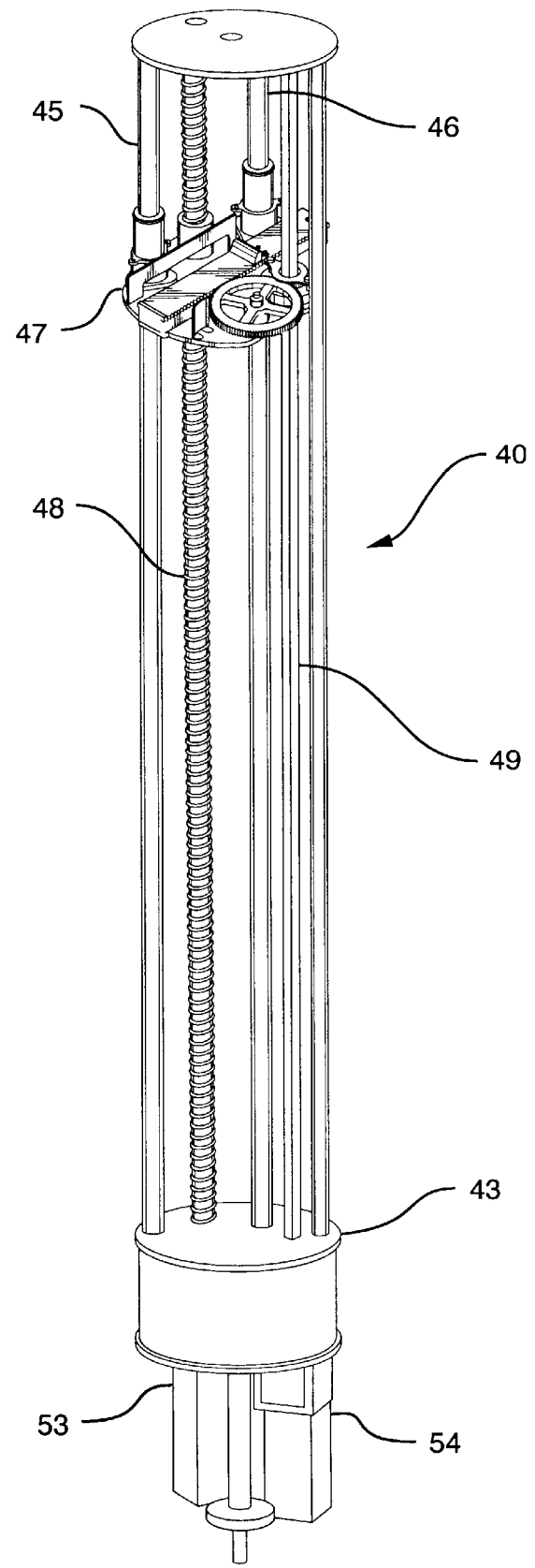

Next, details of an exemplary embodiment of the interchange mechanism 40 will be discussed, as best shown in FIGS. 11A–11B. In this particular embodiment the interchange mechanism 40 comprises a pair of guide rails 45 and 46 that are located with their axes vertically within the freezer compartment 10 and they extend for a substantial length as required by the discrete heights of the various interchange operations. The guide rails 45 and 46 are slidably mounted on the interchange plate 47. A vertical lead screw 48 having an axis length-wise within the freezer compartment 10 is actuated by a motor 53, located below the freezer compartment, for vertically translating the interchange plate 47 to a desired height. A vertically mounted rotating square shaft 49 is driven by a motor 54 mounted beneath the floor of freezer compartment 10. The square shaft 49 drives the interchange tray 44 using a gear train, such as the square shaft gear 50 and tray gear 51, as shown. The drive gear mates with a rack 52 in communication with the interchange tray 44. During operation, the square shaft 49 rotates in a clockwise direction to drive the gear train and rack 52, thereby driving the interchange tray 44 horizontally into an extended position, as shown by the dashed lines. While in the extended position, the interchange tray 44 is capable of retrieving or dropping off a container. Next, the square shaft 49 rotates in a counter-clockwise direction to drive the gear train and rack 52 in an opposite direction, causing the rack 52 and interchange tray 44 to retract to a rest position. The rotary transporter 43, driven by a motor (not shown) mounted beneath the floor of the freezer compartment 10, rotates the interchange mechanism 40 to rotationally align with correct vertical rack 23 or stationary storage rack 26, 26, and interior door 61 of the chamber 60, or any other position as required. The rotary transporter 43 may be pivoted, rotated, or translated using a means known to those skilled in the art.

It should be noted that the motors for the storage carousel 10, vertical transporter 42, rotary transporter 43, picking mechanism 42, and transport tray 63 can be a variety of types of motors known to those skilled in the art, including but not limited thereto servo motors and stepper motors, or any direct current (DC) motor with suitable position or velocity controllers. In the various preferred embodiments disclosed herein, the motors are mounted outside of the freezer compartment 10 to extend the life of the component and improve the overall serviceability of the apparatus. With the exception of the transport tray 63 the drive shafts are mounted through a series of sophisticated thermal seals and thermal couplers designed to maintain temperature stability throughout all operating cycles. In a choice embodiment, the servomotors may be of a SMART MOTOR by Antimatics, Corp. These type of servo motors are microprocessor controlled, ensuring accurate placement and monitoring of the robotics operating within the critical environment; however, any position or velocity controlled motors may be used.

Figure 12:
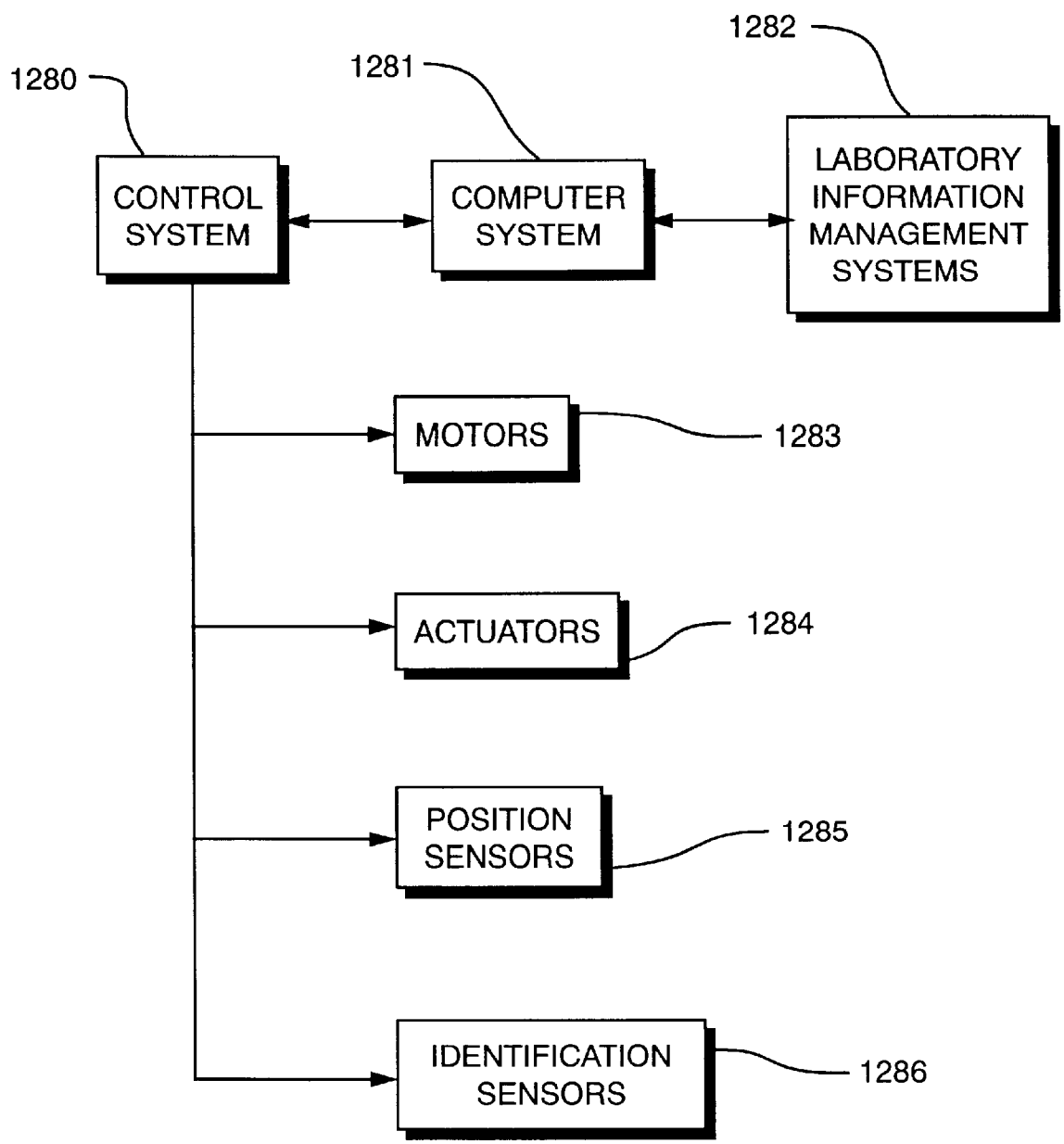
FIG. 12 shows a schematic block diagram of the general features of the control system of the automated storage and retrieval apparatus.

Next, the general features of the present invention control system 1280 will be discussed, as shown in the block diagram of FIG. 12. The control system 1280 interfaces with a computer system 1281 that may be integral with the housing 2 or remote via a wire or wireless communication, or any combination thereof. Moreover, the control system 1280 may be in communication with and integrated with a laboratory information management system (LIMS) 1282. The control system 1280 is operatively connected with the various motors 1283, actuators 1284, position sensors 1285, and identification sensors 1286. It is contemplated that that the information derived from the sample or work pieces carried in the containers 3 while practicing the present invention will provide an information technology platform for the user. The computer system 1281 is intended to be a user-friendly, utilizing Windows-based platform or any other operating system, and may be integrated with a variety of laboratory information management systems. It is envisioned that the control system 1280 and computer system 1281 can be accessed directly by using a touch screen interface or remotely by a stand alone personal computer or with a local area network (LAN).

The present invention apparatus provides the user the capability, among other things, to set top-level user-definable parameters to control container (sample) access based on research groups, research campaigns or individual laboratories. For instance, sample data can be configured by the user to meet the user's particular research requirements. The database can then search the user's sample populations to find all the samples that match the user's requested research parameters. Moreover, time/temperature profiles and sample access histories are maintained continuously. The present invention allows the user to set sample migration thresholds. This feature, employing sample usage frequencies, prompts the movement of low demand samples into longer-term storage units—maximizing the efficiency of the user's sample process management system. Furthermore, the present invention apparatus enables the user to generate a variety of reports in support of the user's quality assurance needs. Finally, the user will benefit from the present invention's information technology by receiving excellent sample security, optimal sample visibility, optimal quality assurance, sample migration control and flexible data management.

Figure 13:
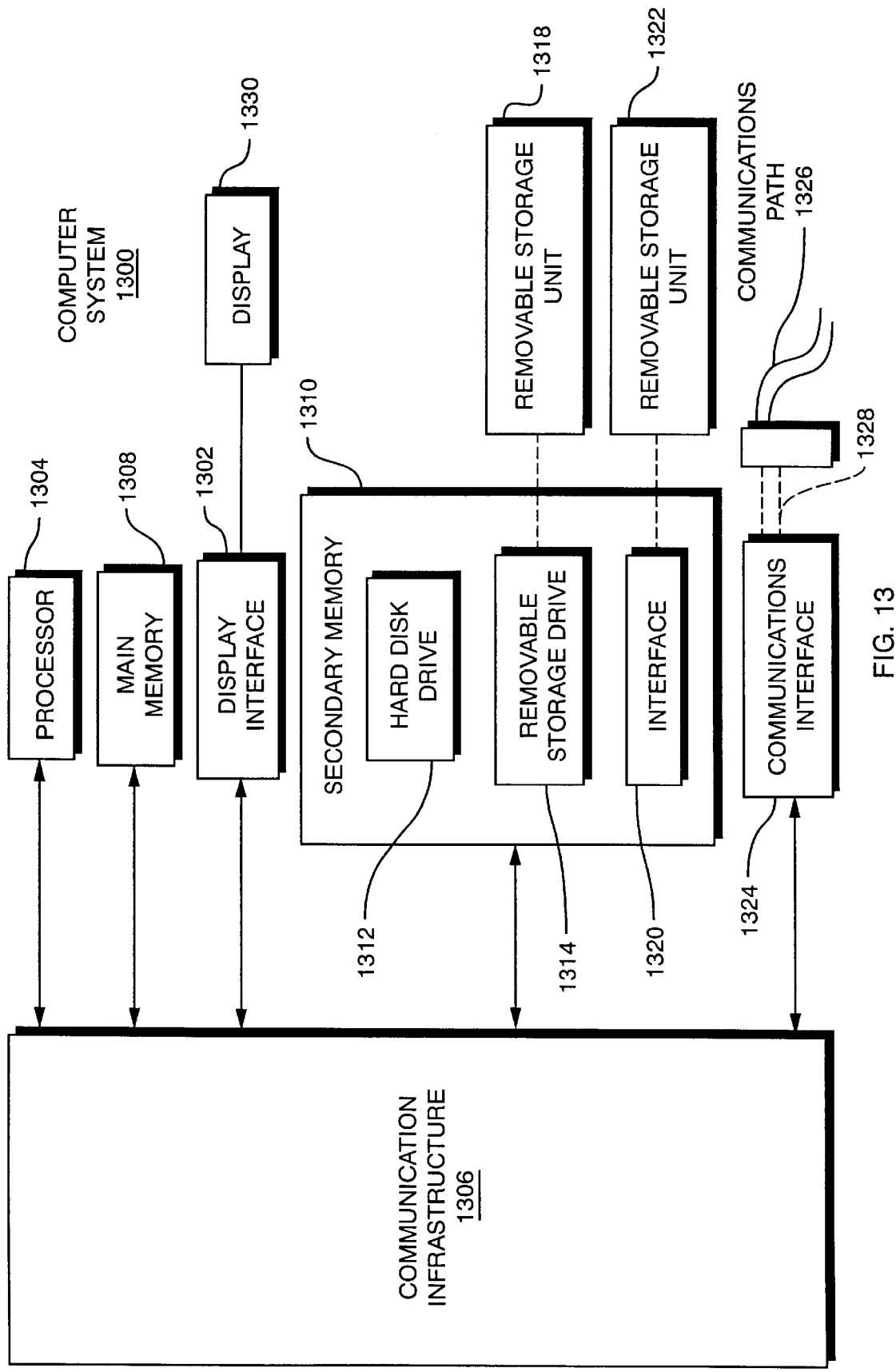
FIG. 13 shows a schematic block diagram of an exemplary computer system associated with an embodiment of the automated storage and retrieval apparatus.

Next, exemplary embodiments of the control system and computer system will be discussed, as best shown in FIG. 13. The controls and processing of present invention may be implemented using hardware, software or a combination thereof and may be implemented in one or more computer systems or other processing systems, such as personal digit assistants (PDAs). In an example embodiment, the invention was implemented in software running on a general purpose computer 1300 as illustrated in FIG. 1300. Computer system 1300 includes one or more processors, such as processor 1304. Processor 1304 is connected to a communication infrastructure 1306 (e.g., a communications bus, cross-over bar, or network). Computer system 1300 includes a display interface 1302 that forwards graphics, text, and other data from the communication infrastructure 1306 (or from a frame buffer not shown) for display on the display unit 1330.

Computer system 1300 also includes a main memory 1308, preferably random access memory (RAM), and may also include a secondary memory 1310. The secondary memory 1320 may include, for example, a hard disk drive 1312 and/or a removable storage drive 1314, representing a floppy disk drive, a magnetic tape drive, an optical disk drive, etc. The removable storage drive 1314 reads from and/or writes to a removable storage unit 1318 in a well known manner. Removable storage unit 1318, represents a floppy disk, magnetic tape, optical disk, etc. which is read by and written to by removable storage drive 1314. As will be appreciated, the removable storage unit 1318 includes a computer usable storage medium having stored therein computer software and/or data.

In alternative embodiments, secondary memory 1310 may include other means for allowing computer programs or other instructions to be loaded into computer system 1300. Such means may include, for example, a removable storage unit 1322 and an interface 1320. Examples of such removable storage units/interfaces include a program cartridge and cartridge interface (such as that found in video game devices), a removable memory chip (such as a ROM, PROM, EPROM or EEPROM) and associated socket, and other removable storage units 1322 and interfaces 1320 which allow software and data to be transferred from the removable storage unit 1322 to computer system 1300.

Computer system 1300 may also include a communications interface 1324. Communications interface 1324 allows software and data to be transferred between computer system 1300 and external devices. Examples of communications interface 1324 may include a modem, a network interface (such as an Ethernet card), a communications port, a PCMCIA slot and card, etc. Software and data transferred via communications interface 1324 are in the form of signals 1328, which may be electronic, electromagnetic, optical or other signals capable of being received by communications interface 1324. Signals 1328 are provided to communications interface 1324 via a communications path (i.e., channel) 1326. A channel 1326 (or any other communication means or channel disclosed herein) carries signals 1328 and may be implemented using wire or cable, fiber optics, a phone line, a cellular phone link, an RF link and other communications channels.

In this document, the terms "computer program medium" and "computer usable medium" are used to generally refer to media such as removable storage drive 1314, a hard disk installed in hard disk drive 1312, and signals 1328. These computer program products are means for providing software to computer system 1300. The invention includes such computer program products.

Computer programs (also called computer control logic) are stored in main memory 1308 and/or secondary memory 1310. Computer programs may also be received via communications interface 1324. Such computer programs, when executed, enable computer system 1300 to perform the features of the present invention as discussed herein. In particular, the computer programs, when executed, enable processor 1304 to perform the functions of the present invention. Accordingly, such computer programs represent controllers of computer system 1300.

In an embodiment where the invention is implemented using software, the software may be stored in a computer program product and loaded into computer system 1300 using removable storage drive 1314, hard drive 1312 or communications interface 1324. The control logic (software), when executed by the processor 1304, causes the processor 1304 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in VISUAL BASIC control language, but could be implemented in other programs such as, but not limited to, C++ programming language.

Figure 14A:
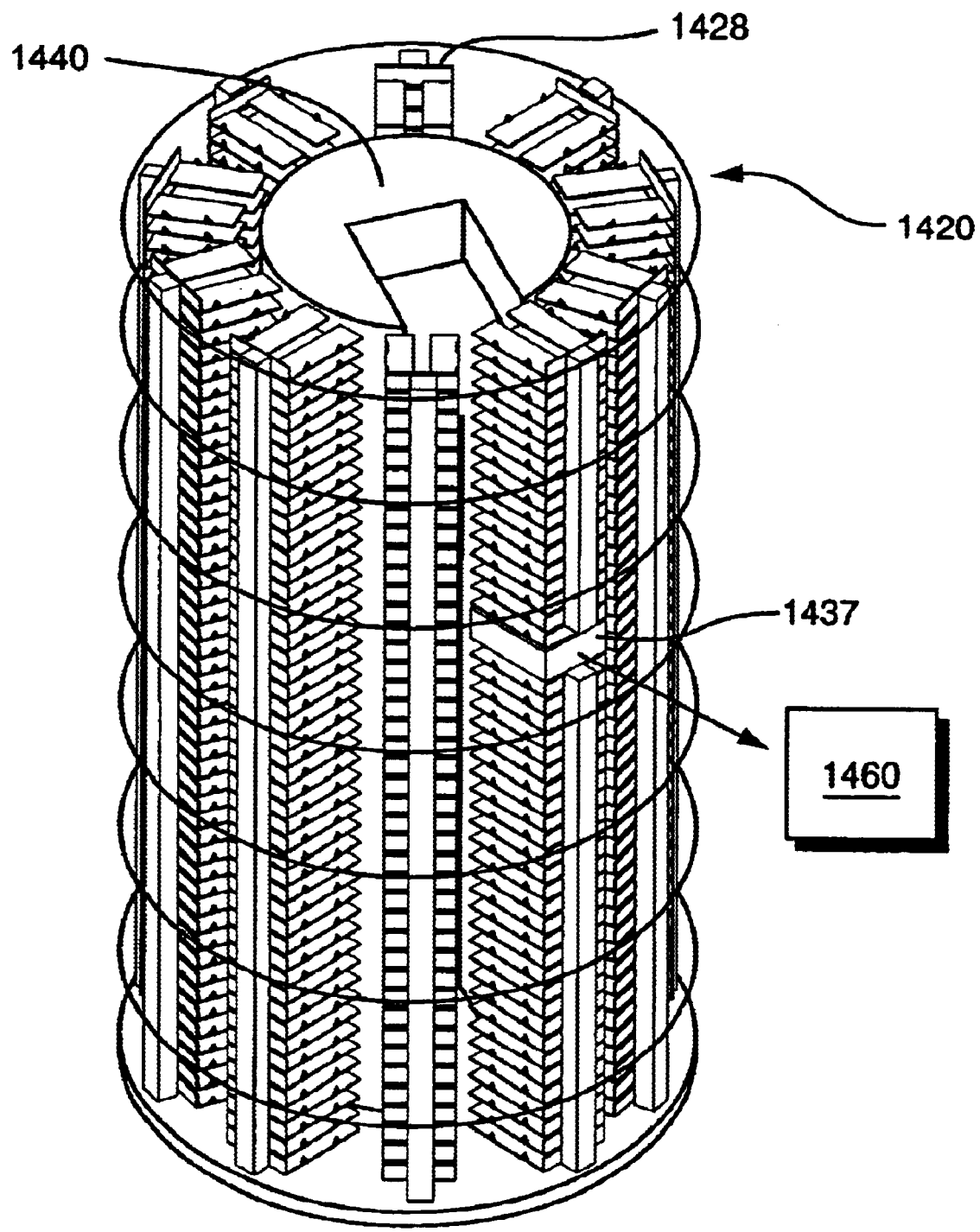
FIGS. 14A and 14B show schematic perspective views of an alternative embodiment of the automated storage and retrieval apparatus.
Figure 14B:
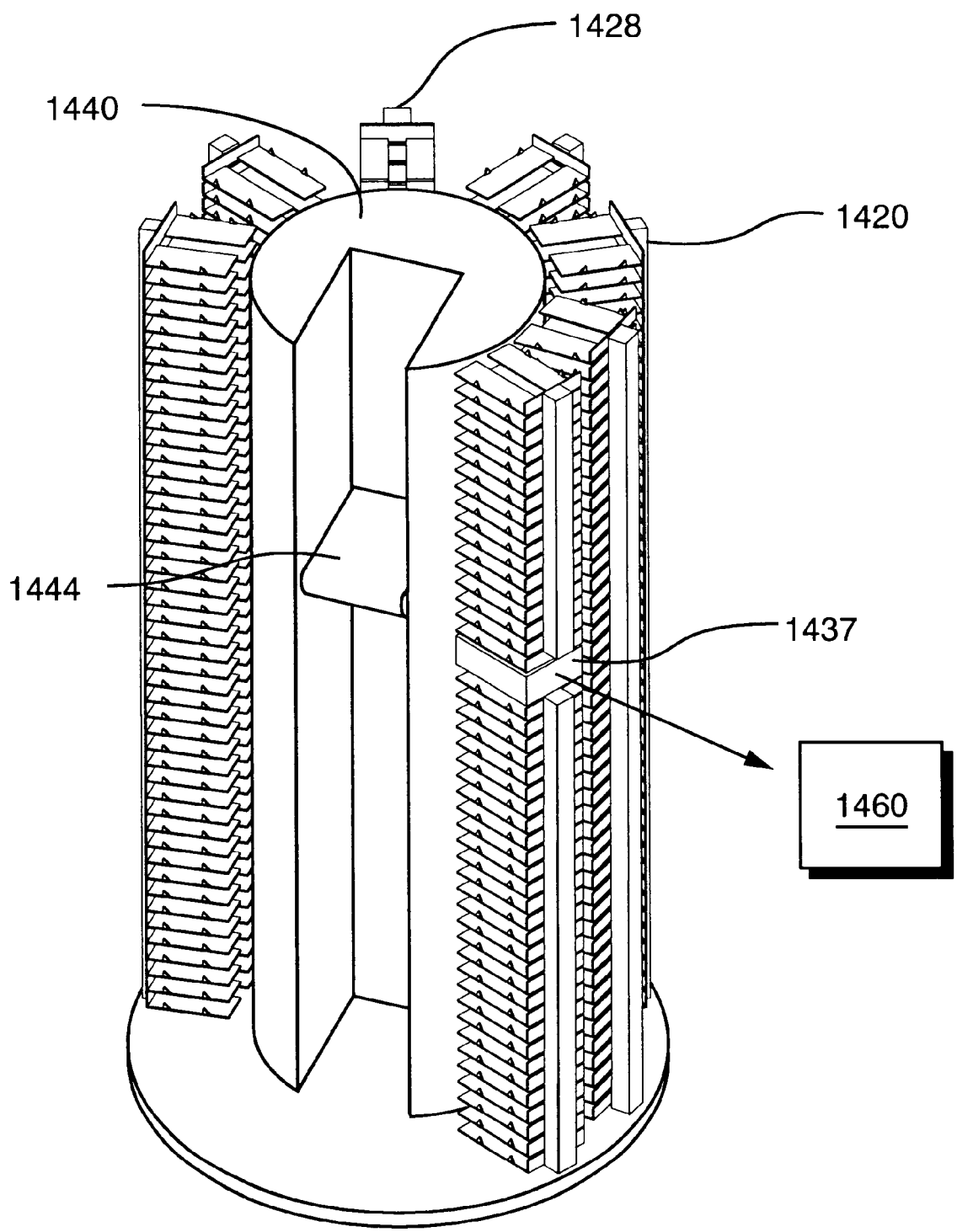

Next, details of an alternative second embodiment of the present invention will be discussed, as best shown in FIGS. 14A–B. The storage carousel is fixed in place (i.e., no rotation) providing a fixed hotel 1420. The storage containers 1403 are accommodated on shelves 1428 in the same manner as in the storage carousel. However, the interchange mechanism 1440 is located in the central core 1439 of the fixed hotel 1420. The interchange mechanism 1440 includes an interchange tray 1444, and may rotate about its axis and travel vertically as previously discussed herein. The interchange mechanism 1440 retrieves storage containers from shelves, takes them to a vertical position aligned with an access portal 1437, and moves them through the portal 1437 to the exterior of the freezer via the climate controlled chamber 1460. It is noted that the access portal 1437 is a fixed hole in the fixed hotel 1420 allowing samples to access the interchange mechanism 1440. One or more access portals may be used if one wishes to mate several fixed hotels 1420 or rotating carousels together, or provide more than one point of access portal 1437. Furthermore, the access portal may be movable if one wishes to provide rotational movement to one "slice" of the hotel 1420.

An advantage of this second embodiment approach, but not limited thereto is that it may be accommodated in a cylindrical freezer compartment, occupying less space. In addition, this apparatus and method obviates the need for a rotational mechanism for the carousel (unless one wishes to have a movable access port). All other aspects of the design are the same as previously described above.

In addition, as a third alternative embodiment, one could also have a second carousel outside the one depicted in FIGS. 14A–14B, so as to allow for greater storage space. In this embodiment the inside carousel could rotate so as to allow a vertical arrangement and rotational alignment of access ports to access any compartment in the outer carousel.

Next, details of providing an expanded network system of cooperating freezer apparatuses 1501 will be discussed, as best shown n FIGS. 15A-D. The plurality storage of carousels 1520 (or stationary storage racks 1526, 1527 and fixed hotels), interchange mechanism 1540, and climate control chamber 1560 operate with the methods and aspects described herein. The plurality of storage carousels 1520 (stationary racks or fixed hotels) operates in an enclosure 1502. The enclosure 1502 may be equipment housing-type as previously discussed to accommodate a freezer unit or plurality of freezer units. Alternatively, the enclosure 1502 may be an entire room, or a plurality of rooms, as disclosed in the U.S. Pat. No. 5,921,102 Vago patent. The configurations shown in FIGS. 15A–D are illustrative in nature and are not intended to be exhaustive as other combinations and designs are contemplated. Essentially, the containers 1503 are interchanged, stored, deposited, and retrieved among the storage carousels 1520 (including stationary storage racks 1526, 1527), interchange mechanism 1540, and climate-controlled chamber 1560 using the aspects and methods previously disclosed herein, while recognizing the enclosure 1502 may be a room or equipment housing, or any combination thereof. A control system 1580 is operatively connected to the various components and subsystems, wherein the controls and processor are locally or remotely located.

Figure 15A:
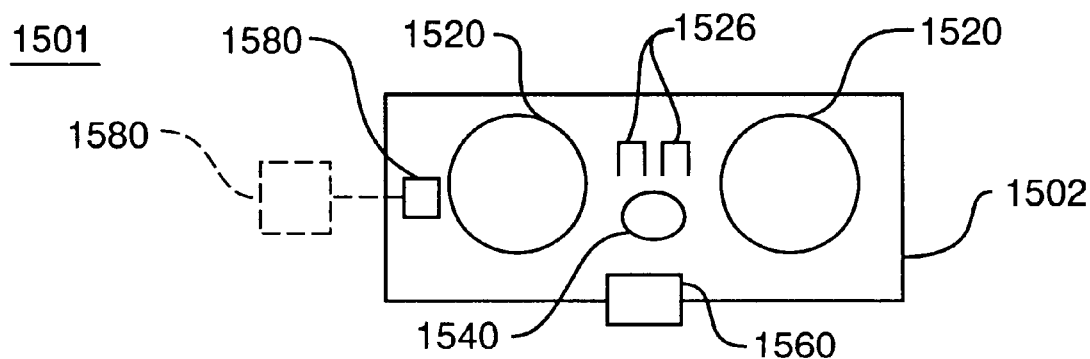
FIGS. 15A–15D show schematic plan views of an alternative embodiment of the automated storage and retrieval apparatus providing expanded network system of cooperating freezer apparatuses.
Figure 15B:
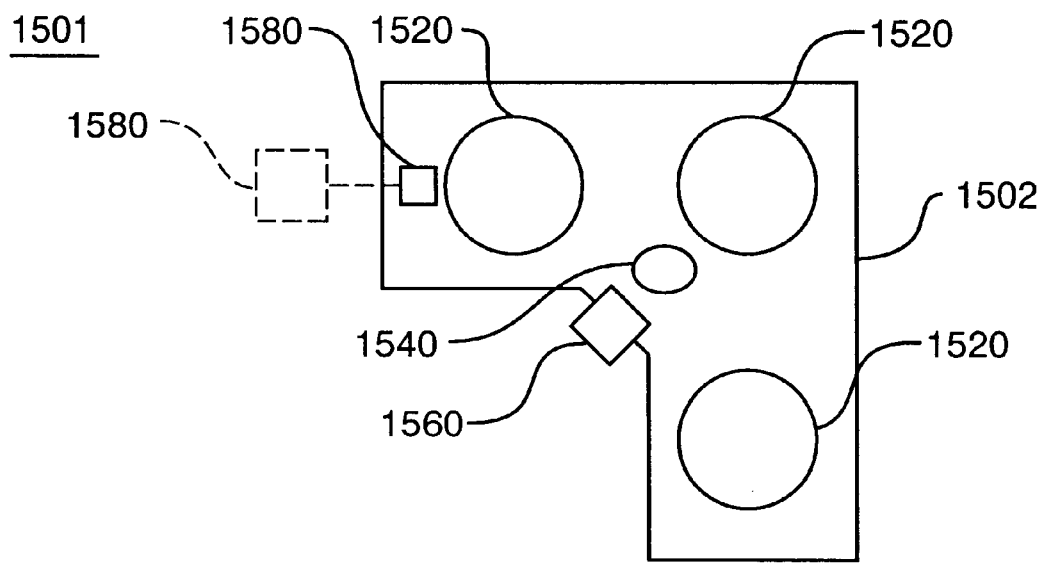
Figure 15C:
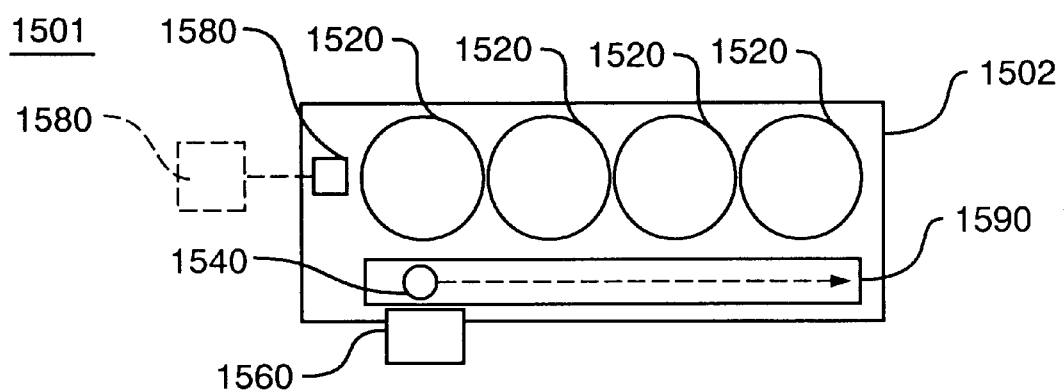
Figure 15D:
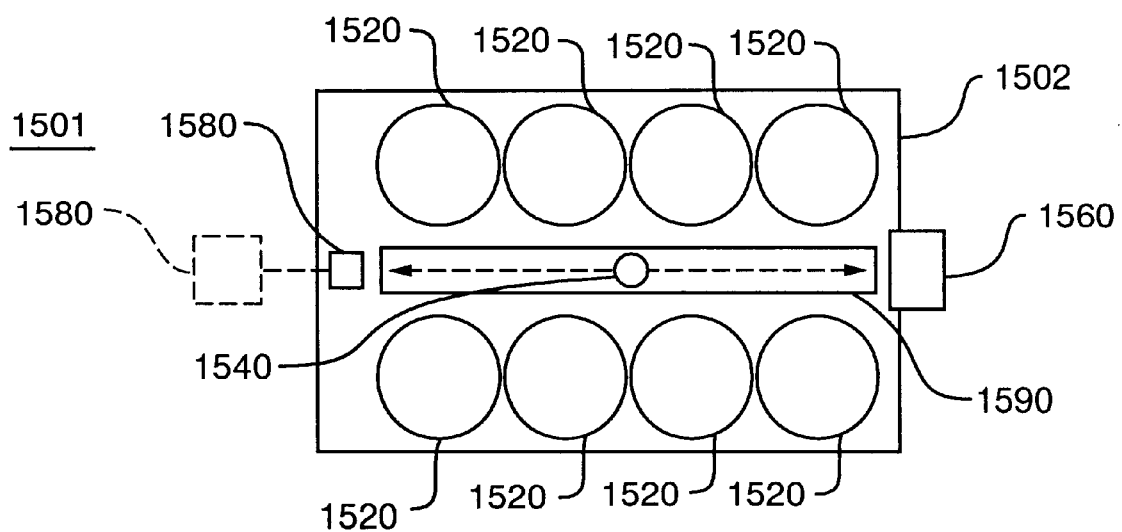

The interchange mechanism 1540 cooperate with multiple locations allowing containers 1503 to pass among carousels 1520 and stationary racks 1526, 1527, and of course the climate-controlled chamber 1560. As shown in FIGS. 15C–D, to accomplish this task, a translating mechanism 1590 is provided to translate or shift the interchange mechanism 1540 to the target carousel(s) 1520 or stationary racks 1526, 1527. Various means are contemplated for translating the interchange mechanism 1540, including but not limited thereto, track devices, wheels, conveyors, pulleys, suspension devices, belts, gears, or other robotic devices.

Some advantages of the present invention automated storage and retrieval apparatus for ultra low temperature freezers, and related method thereof, are that it provides a more organized storage and retrieval apparatus, less accumulation of moisture and frost within the cold storage compartment, less temperature fluctuation from sample withdrawal, and rapid random access to all specimens.

Moreover, another advantage of the present invention is that the apparatus can operate in a stand-alone mode or can be integrated into a completely automated laboratory. It is scalable to meet the needs of small laboratories as well as large institutions that will require long-term storage of large numbers of samples.

Another advantage of the present invention is that the apparatus can be designed as a slide-in unit for existing ultra-cold freezers, which will keep the majority of the hardware in the door so as to be insulated from the freezer compartment, minimizing both the number of low-temperature hardware components and the actual alteration to the freezer itself. A reduced number of moving component is continuously exposed to the normal design temperature of about −80° C., reducing the cost of production.

Further advantages of the present invention are attributed to the improved sample quality, lowered operating costs, and reduced maintenance of the automated storage and retrieval apparatus.

Still further, an advantage of the present invention is that the climate-controlled chamber prevents ambient, humid air from entering the interior of freezer compartment during storage container insertion and retrieval.

Finally, an advantage of the present invention is that it provides ultra-low temperature automation and user-friendly information technology in a proven reliable manner. It is contemplated that the present invention apparatus may provide an operation temperature below and above the ultra low operating temperature.

The invention may be embodied in other specific forms without departing from the spirit or essential characteristics thereof. The foregoing embodiments are therefore to be considered in all respects illustrative rather than limiting of the invention described herein. Scope of the invention is this indicated by the appended claims rather than by the foregoing description, and all changes which come within the meaning and range of equivalency of the claims are therefore intended to be embraced herein.

We claim:

1. An automated storage and retrieval apparatus for storing containers at ultra low temperatures, said apparatus comprising:

a freezer compartment, said freezer compartment having a side wall;

a storage carousel disposed inside said freezer compartment for holding the containers;

a climate-controlled chamber disposed on said side wall;

a climate system for controlling the climate of said chamber;

an interchange mechanism disposed inside said storage carousel configured to:
interchange a container between said interchange mechanism and said climate-controlled chamber while in a chamber exchange position, and
interchange a container between said interchange mechanism and said carousel while in a carousel exchange position; and said chamber being configured to:
isolate the container from said interchange mechanism as container is deposited from the exterior or placed into the exterior, and
isolate the container from the exterior as container is exchanged between said chamber and said interchange mechanism.

2. The apparatus of claim 1, wherein said chamber further comprises:

an exterior door, whereby said exterior door is adapted to allow the containers to interchange between said chamber and the exterior, and an interior door, whereby said interior door is adapted to allow the containers to interchange between said chamber and said interchange mechanism.

3. The apparatus of claim 1, where said chamber further comprises:

a transport tray slidably mounted to said chamber for transporting the container between an outer position closest to the exterior and an interior position closest to said interchange mechanism.

4. The apparatus of claim 3, wherein said controlled chamber further comprises:
   a motor operably connected to said transport tray for translating said tray between the exterior position and interior position, and any position generally there between; and
   said motor being disposed outside said freezer compartment.

5. The apparatus of claim 1, wherein said climate system comprises a dry gas supply to dehumidify said chamber and cool said chamber.

6. The apparatus of claim 1, wherein said chamber comprises a writing device.

7. The apparatus of claim 1, wherein said chamber comprises a reading device to identify the containers as they are inserted into and retrieved from said chamber.

8. The apparatus of claim 1, further comprising a control system, wherein said control system is operatively connected with said carousel, said interchange mechanism, and chamber for controlling their operations.

9. The apparatus of claim 8, wherein said control system comprises a processor for processing data relative to the containers being stored in and retrieved from the apparatus.

10. The apparatus of claim 8, wherein said control system comprises a processor for processing data relating to contents of the containers being stored in and retrieved from the apparatus.

11. The apparatus of claim 8, further comprising a user station operatively connected to the apparatus, said user station comprising a data input means for inputting data to said processor relative to the containers.

12. The apparatus of claim 1, wherein said interchange mechanism further comprises:
   an interchange tray configured to retain the container.

13. The apparatus of claim 12, wherein said interchange mechanism comprises:
   a picking mechanism translating said interchange tray for interchanging the container with said carousel or said chamber.

14. The apparatus of claim 12, wherein said interchange mechanism further comprises:
   a vertical transporter configured to allow said interchange mechanism to be translated vertically over a plurality of discrete heights.

15. The apparatus of claim 14, wherein said interchange mechanism further comprises:
   a rotary transporter, said rotary transporter configured to rotate said interchange mechanism to a plurality of discrete circumferential positions.

16. The apparatus of claim 15, wherein said circumferential positions include rotational alignment corresponding to a position at which the interchange mechanism can:
   interchange selected containers with said climate-controlled chamber while in the chamber exchange position; and
   interchange selected containers with said carousel while in the carousel exchange position.

17. The apparatus of claim 15, further comprises:
   a motor operably connected to said rotary transporter for rotating said interchange mechanism the plurality of discrete circumferential orientations; and
   said motor being disposed outside said freezer compartment.

18. The apparatus of claim 14, wherein said discrete heights include the heights corresponding to a height at which the interchange mechanism can:
   interchange selected containers with said climate-controlled chamber while in the chamber exchange position; and
   interchange selected containers with said carousel while in the carousel exchange position.

19. The apparatus of claim 14, further comprises:
   a motor operably connected to said vertical transporter for vertically translating said interchange mechanism to discrete heights; and
   said motor being disposed outside said freezer compartment.

20. The apparatus of claim 12, further comprises:
   a motor operably connected to said picking mechanism for substantially horizontally translating said picking mechanism between an extended position for use during the interchanging of the container, and a retracted position while the container remains in the non-extended position; and
   said motor being disposed outside said freezer compartment.

21. The apparatus of claim 1, wherein said carousel further comprises an annular ring of vertical racks arranged circumferentially.

22. The apparatus of claim 21, wherein said carousel further comprises storage trays to hold a plurality of storage containers.

23. The apparatus of claim 22, wherein said storage trays are adjustably mounted.

24. The apparatus of claim 21, wherein said carousel further comprises an upper horizontal top plate and a lower horizontal support plate.

25. The apparatus of claim 21, wherein said carousel is rotatable so as to align said vertical racks with said interchange mechanism.

26. The apparatus of claim 21, wherein said carousel is stationary.

27. The apparatus of claim 21, further comprising:
   a motor operably connected to said carousel for rotating said carousel; and
   said motor being disposed outside said freezer compartment.

28. The apparatus of claim 1, further comprising:
   at least one access portal disposed on said carousel.

29. The apparatus of claim 28, wherein said at least one access portal is adapted to allow selected containers to pass there through when said selected containers are passed between said chamber and said interchange mechanism.

30. An automated storage and retrieval apparatus for storing containers at ultra low temperatures, said apparatus comprising:
   a freezer means for freezing the containers;
   a storage means disposed inside said freezer means for holding the containers;
   a chamber means for interchanging the containers between the exterior and said freezer means;
   a climate system control means for controlling the climate of said chamber means;
   an interchange means disposed inside said storage means for:
      interchanging a container between said interchange means and said chamber means while in a chamber exchange position, and interchanging a container between said interchange means and said storage means while in a storage exchange position; and said chamber means for:
isolating the container from said interchange means as container is deposited from the exterior or placed into the exterior, and
isolating the container from the exterior as container is exchanged between said chamber means and said interchange means.

31. An automated storage and retrieval apparatus for storing containers at ultra low temperatures, said apparatus comprising:
a freezer compartment, said freezer compartment having a side wall;
a storage device disposed inside said freezer compartment for holding the containers;
a climate-controlled chamber disposed on said side wall;
a climate system for controlling the climate of said chamber;
an interchange mechanism disposed inside said storage device configured to:
interchange a container between said interchange mechanism and said climate-controlled chamber while in a chamber exchange position, and
interchange a container between said interchange mechanism and said storage device while in a device exchange position; and
said chamber being configured to:
isolate the container from said interchange mechanism as container is deposited from the exterior or placed into the exterior, and
isolate the container from the exterior as container is exchanged between said chamber and said interchange mechanism.

32. The apparatus of claim 31, wherein said storage device is movable so as to align said storage device with said interchange mechanism.

33. The apparatus of claim 31, wherein said storage device is stationary.

34. The apparatus of claim 31, further comprising:
at least one access portal disposed on said carousel.

35. The apparatus of claim 34, wherein said at least one access portal is adapted to allow selected containers to pass there through when said selected containers are passed between said chamber and said interchange mechanism.

36. A method for automatically depositing and storing containers in a freezer compartment at ultra low temperatures, said method comprising:
providing a carousel in said freezer compartment;
providing an interchange mechanism disposed inside said carousel;
depositing a container into a climate-controlled chamber;
controlling the climate of said chamber while isolating said chamber for a predetermined time while the container remains in said chamber;
retrieving the container from said chamber to said freezer compartment with said interchange mechanism while said chamber is isolated from the exterior; and
storing the container in said carousel.

37. A method for automatically storing and retrieving containers in a freezer compartment at ultra low temperatures, said method comprising:

providing a carousel in said freezer compartment;
providing an interchange mechanism disposed inside said carousel; providing a climate controlled chamber;
retrieving a stored container from said carousel into said climate controlled chamber with said interchange mechanism, while said chamber is isolated from the exterior;
controlling the climate of said chamber while isolating said chamber for a predetermined time while the container remains in said chamber; and
presenting the container for pickup while said chamber is isolated from said freezer compartment.

38. The method of claim 37, wherein said presenting the container comprises ejecting the container to the exterior for pickup.

39. A method for automatically depositing and storing containers in a freezer compartment of an automated apparatus at ultra low temperatures, said apparatus comprising:
a freezer compartment, said freezer compartment having a side wall;
a storage carousel disposed inside said freezer compartment for holding the containers;
a climate-controlled chamber disposed on said side wall;
a climate control system for controlling the climate of said chamber;
an interchange mechanism disposed inside said storage carousel configured to:
interchange a container between said interchange mechanism and said climate-controlled chamber while in a chamber exchange position, and
interchange a container between said interchange mechanism and said carousel while in a carousel exchange position; and
said chamber being configured to:
isolate the container from said interchange mechanism as container is deposited from the exterior or placed into the exterior, and
isolate the container from the exterior as container is exchanged between said chamber and said interchange mechanism.

40. A method for automatically storing and retrieving containers in a freezer compartment of an automated apparatus at ultra low temperatures, said apparatus comprising:
a freezer compartment, said freezer compartment having a side wall;
a storage carousel disposed inside said freezer compartment for holding the containers;
a climate-controlled chamber disposed on said side wall;
a climate control system for controlling the climate of said chamber;
an interchange mechanism disposed inside said storage carousel configured to:
interchange a container between said interchange mechanism and said climate-controlled chamber while in a chamber exchange position, and
interchange a container between said interchange mechanism and said carousel while in a carousel exchange position; and
said chamber being configured to:
isolate the container from said interchange mechanism as container is deposited from the exterior or placed into the exterior, and
isolate the container from the exterior as container is exchanged between said chamber and said interchange mechanism.

41. A method for automatically depositing and storing containers in a freezer compartment of an automated apparatus at ultra low temperatures, said apparatus comprising:
- a freezer means for freezing the containers;
- a storage means disposed inside said freezer means for holding the containers;
- a chamber means for interchanging the containers between the exterior and said freezer means;
- a climate system control means for controlling the climate of said chamber means;
- an interchange means disposed inside said storage means for:
  - interchanging a container between said interchange means and said chamber means while in a chamber exchange position, and
  - interchanging a container between said interchange means and said storage means while in a storage exchange position; and
- said chamber means for:
  - isolating the container from said interchange means as container is deposited from the exterior or placed into the exterior, and
  - isolating the container from the exterior as container is exchanged between said chamber means and said interchange means.

42. A method for automatically storing and retrieving containers in a freezer compartment of an automated apparatus at ultra low temperatures, said apparatus comprising:
- a freezer means for freezing the containers;
- a storage means disposed inside said freezer means for holding the containers;
- a chamber means for interchanging the containers between the exterior and said freezer means;
- a climate system control means for controlling the climate of said chamber means;
- an interchange means disposed inside said storage means for:
  - interchanging a container between said interchange means and said chamber means while in a chamber exchange position, and
  - interchanging a container between said interchange means and said storage means while in a storage exchange position; and
- said chamber means for:
  - isolating the container from said interchange means as container is deposited from the exterior or placed into the exterior, and
  - isolating the container from the exterior as container is exchanged between said chamber means and said interchange means.

* * * * *